(12) United States Patent
Irimia et al.

(10) Patent No.: US 11,130,132 B2
(45) Date of Patent: Sep. 28, 2021

(54) MICROFLUIDIC NEUTROPHIL ASSAYS AND SYSTEMS FOR DISEASE DETECTION

(71) Applicant: The General Hospital Corporation, Boston, MA (US)

(72) Inventors: Daniel Irimia, Charlestown, MA (US); Felix Ellett, Jamaica Plain, MA (US); Julianne Jorgensen, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 190 days.

(21) Appl. No.: 16/099,117

(22) PCT Filed: May 8, 2017

(86) PCT No.: PCT/US2017/031557
§ 371 (c)(1),
(2) Date: Nov. 5, 2018

(87) PCT Pub. No.: WO2017/193126
PCT Pub. Date: Nov. 9, 2017

(65) Prior Publication Data
US 2019/0143326 A1    May 16, 2019

Related U.S. Application Data

(60) Provisional application No. 62/332,659, filed on May 6, 2016, provisional application No. 62/418,562, filed on Nov. 7, 2016.

(51) Int. Cl.
*B01L 3/00* (2006.01)
*G01N 33/50* (2006.01)
(Continued)

(52) U.S. Cl.
CPC .... *B01L 3/502753* (2013.01); *G01N 15/0205* (2013.01); *G01N 15/1031* (2013.01);
(Continued)

(58) Field of Classification Search
None
See application file for complete search history.

(56) References Cited

U.S. PATENT DOCUMENTS

| 5,744,366 A | 4/1998 | Kricka et al. |
| 6,238,874 B1 | 5/2001 | Jarnagin et al. |

(Continued)

FOREIGN PATENT DOCUMENTS

| WO | WO 02/44730 | 6/2002 |
| WO | WO 2009/102453 | 8/2009 |

(Continued)

OTHER PUBLICATIONS

Agrawal et al., "Neutrophil migration assay from a drop of blood," Lab Chip., 8(12):2054-2061, Epub Oct. 30, 2008.
(Continued)

*Primary Examiner* — Xiaoyun R Xu
(74) *Attorney, Agent, or Firm* — Fish & Richardson P.C.

(57) ABSTRACT

The disclosure relates to microfluidic devices and methods of use thereof for monitoring the directionality, velocity, and migration persistence of neutrophils or other cells in the absence of chemical gradients for the purposes of detecting and quantifying abnormal neutrophil motility phenotypes, using low sample volumes and with minimal activation of the neutrophils. The devices and methods can be used to diagnose sepsis in subjects suspected of having sepsis or at risk of developing sepsis. The devices and methods can also be used to monitor the responses of patients to sepsis therapies.

19 Claims, 10 Drawing Sheets

(51) Int. Cl.
*G01N 33/543* (2006.01)
*G01N 15/14* (2006.01)
*G01N 15/02* (2006.01)
*G01N 15/10* (2006.01)
*G01N 33/487* (2006.01)

(52) U.S. Cl.
CPC ..... *G01N 15/1056* (2013.01); *G01N 15/1459* (2013.01); *G01N 15/1463* (2013.01); *G01N 15/1484* (2013.01); *G01N 33/487* (2013.01); *G01N 33/5091* (2013.01); *G01N 33/54366* (2013.01); *B01L 2200/0694* (2013.01); *B01L 2300/0864* (2013.01); *B01L 2300/0867* (2013.01); *B01L 2400/086* (2013.01); *G01N 2015/1006* (2013.01); *G01N 2015/1075* (2013.01); *G01N 2015/1488* (2013.01); *G01N 2015/1493* (2013.01); *G01N 2800/26* (2013.01)

(56) References Cited

U.S. PATENT DOCUMENTS

| | | | |
|---|---|---|---|
| 6,921,660 | B2 | 7/2005 | Kirk et al. |
| 7,326,563 | B2 | 2/2008 | Enoch et al. |
| 7,374,906 | B2 | 5/2008 | Kirk et al. |
| 8,921,122 | B2 | 12/2014 | Irimia |
| 2002/0168757 | A1 | 11/2002 | Kirk et al. |
| 2005/0271548 | A1 | 12/2005 | Yang et al. |
| 2007/0264675 | A1 | 11/2007 | Toner et al. |
| 2011/0117579 | A1 | 5/2011 | Irimia |
| 2011/0124025 | A1 | 5/2011 | Castrocane et al. |
| 2012/0094325 | A1 | 4/2012 | Irimia |
| 2012/0216601 | A1 | 8/2012 | Irimia |
| 2012/0315660 | A1 | 12/2012 | Schroeder et al. |
| 2013/0244270 | A1 | 9/2013 | Xie et al. |

FOREIGN PATENT DOCUMENTS

| | | |
|---|---|---|
| WO | WO 2010/036913 | 4/2010 |
| WO | WO 2010/108095 | 9/2010 |
| WO | WO 2015/042436 | 3/2015 |

OTHER PUBLICATIONS

Albini and Benelli "The chemoinvasion assay: a method to assess tumor and endothelial cell invasion and its modulation," Nat Protoc. 2(3):504-511 (2007).
Beningo et al. "Responses of fibroblasts to anchorage of dorsal extracellular matrix receptors," Proc Natl Acad Sci USA 101(52):18024-18029 (2004).
Bovin and Gabius "Polymer-immobilized carbohydrate ligands. Versatile Chemical Tools for Biochemistry and Medical Sciences," Chemical Society Reviews 24(6):413-421 (1995).
Boyden "The Chemotactic Effect of Mixtures of Antibody and Antigen on Polymorphonuclear Leucocytes," Journal of Experimental Medicine 115 (3):453-466 (1962).
Brandley and Schnaar "Cell-Surface Carbohydrates in Cell Recognition and Response," Journal of Leukocyte Biology 40:97-111 (1986).
Buffone et al., "Neutrophil function in surgical patients. Relationship to adequate bacterial defenses," Arch Surg., 119(1):39-43, Jan. 1984.
Butler et al., "Burn injury reduces neutrophil directional migration speed in microfluidic devices," PLoS One., 5(7):e11921, 12 pages, Jul. 30, 2010.
Carmignani et al. "Intraperitoneal cancer dissemination. Mechanisms of the patterns of spread," Cancer Metastasis Rev. 22:465-472 (2003).
Cavallaro and Christofori "Cell adhesion and signalling by cadherins and Ig-CAMs in cancer," Nature Reviews Cancer 4:118-132 (2004).
Chiang and Massague "Molecular Basis of Metastasis" N Engl J Med. 359 (26):2814-2823 (2008).
Condeelis and Segall "Intravital imaging of cell movement in tumours," Nature Reviews Cancer 3:921-930 (2003).
Decaestecker et al. "Can anti-migratory drugs be screened in vitro? A review of 2D and 3D assays for the quantitative analysis of cell migration," Medicinal Research Reviews 27(2):149-176 (2007).
Demou and Mcintire "Fully automated three-dimensional tracking of cancer cells in collagen gels: Determination of motility phenotypes at the cellular level," Cancer Research 62(18):5301-5307.
Even-Ram and Yamada "Cell migration in 3D matrix," Current Opinion in Cell Biology 17:524-532 (2005).
Feki et al. "Dissemination of intraperitoneal ovarian cancer: Discussion of mechanisms and demonstration of lymphatic spreading in ovarian cancer model," Crit Rev Oncol Hematol. 72:1-9 (2009).
Friedl and Wolf "Tumour-cell invasion and migration: Diversity and escape mechanisms," Nature Reviews Cancer 3:362-374 (2003).
Gerhardt and Semb "Pericytes: gatekeepers in tumour cell metastasis?" J Mol Med 86:135-144 (2008).
Giese and Westphal "Glioma invasion in the central nervous system," Neurosurgery 39(2):235-252 (1996).
Hanahan and Weinberg "The Hallmarks of Cancer," Cell 100:57-70 (2000).
Hansson et al., "Inflammation and atherosclerosis," Annu Rev Pathol., 1:297-329, 2006.
Hasenberg et al., "Rapid immunomagnetic negative enrichment of neutrophil granulocytes from murine bone marrow for functional studies in vitro and in vivo," PLoS One, 6(2):e17314, 11 pages, Feb. 23, 2011.
International Preliminary Report on Patentability dated Sep. 29, 2011 issued in International application No. PCT/US2010/027980.
International Preliminary Report on Patentability for PCT/US2014/056614, dated Mar. 31, 2016, 8 pages.
International Preliminary Report on Patentability in International Application No. PCT/US2017/031557, dated Nov. 15, 2018, 8 pages.
International Search Report and Written Opinion dated Oct. 26, 2010 issued in International application No. PCT/US2010/027980.
International Search Report and Written Opinion dated Sep. 28, 2009 from International application No. PCT/US2009/000890.
International Search Report and Written Opinion for PCT/US2014/056614, dated Dec. 30, 2014, 14 pages.
International Search Report and Written Opinion in International Application No. PCT/US2017/031557, dated Sep. 22, 2017, 16 pages.
Irimia et al. "Adaptive-Control Model for Neutrophil Orientation in the Direction of Chemical Gradients," Biophysical Journal 96:3897-3916 (2009).
Irimia et al. "Microfluidic system for measuring neutrophil migratory responses to fast switches of chemical gradients," Lab Chip 6:191-198 (2006).
Irimia et al. "Polar stimulation and constrained cell migration in microfluidic channels," Lab Chip 7:1783-1790 (2007).
Irimia et al. "Universal Microfluidic Gradient Generator," Analytical Chemistry 78(10):3472-3477 (2006).
Irimia et al., "Cell handling using microstructured membranes," Lab Chip., 6(3):345-52. Epub Feb. 8, 2006.
Jones et al., "Microfluidic chambers for monitoring leukocyte trafficking and humanized nano-proresolving medicines interactions," Proc Natl Acad Sci U S A., 109(50):20560-20565, Epub Nov. 26, 2012.
Jones et al., "Spontaneous neutrophil migration patterns during sepsis after major burns," PloS One, 2014, 9(12): e114509.
Keenan and Folch, "Biomolecular gradients in cell culture systems," Lab Chip 8:34-57 (2008).
Keenan et al., "Microfluidic 'jets' for generating steady-state gradients of soluble molecules on open surfaces," Applied Physics Letters 89:114103 (2006) (3 pages).
Kotz et al., "Clinical microfluidics for neutrophil genomics and proteomics," Nat Med., 16(9):1042-1047, Epub Aug. 29, 2010.
Kuntz and Saltzman, "Neutrophil Motility in Extracellular Matrix Gels: Mesh Size and Adhesion Affect Speed of Migration," Biophysical Journal 72:1472-1480 (1997).

(56) References Cited

OTHER PUBLICATIONS

Kurihara et al., "Resolvin D2 restores neutrophil directionality and improves survival after burns," FASEB J., 27(6):2270-2281, Epub Feb. 21, 2013.
Lammermann et al. "Rapid leukocyte migration by integrin-independent flowing and squeezing," Nature 453:51-55 (2008).
Lee et al. "Three-dimensional micropatterning of bioactive hydrogels via two-photon laser scanning photolithography for guided 3D cell migration," Biomaterials 29:2962-2968 (2008).
Levy et al. "Endoscopic ultrasound fine-needle aspiration detection of extravascular migratory metastasis from a remotely located pancreatic cancer," Clin Gastroenterol Hepatol. 7:246-248 (2009).
Lugassy and Barnhill "Angiotropic melanoma and extravascular migratory metastasis: A review," Adv Anat Pathol. 14:195-201 (2007).
Lyons et al., "Microarray analysis of human leucocyte subsets: the advantages of positive selection and rapid purification," BMC Genomics., 8:64, Mar. 5, 2007.
Malawista et al. "Random locomotion and chemotaxis of human blood polymorphonuclear leukocytes from a patient with leukocyte adhesion deficiency-1: Normal displacement in close quarters via chimneying," Cell Motil. Cytoskeleton 46:183-189 (2000).
Mankovich et al., "Differential effects of serum heat treatment on chemotaxis and phagocytosis by human neutrophils," PLoS One., 8(1):e54735, 12 pages, Epub Jan. 22, 2013.
Nauseef, "Isolation of human neutrophils from venous blood," Methods Mol Biol., 412:15-20, 2007.
Office Action in U.S. Appl. No. 13/257,464, dated Aug. 26, 2013, 13 pages.
Office Action in U.S. Appl. No. 13/407,596, dated Mar. 26, 2014, 22 pages.
Office Action in U.S. Appl. No. 15/023,588, dated Feb. 4, 2019, 12 pages.
Office Action in U.S. Appl. No. 15/023,588, dated Jul. 23, 2018, 12 pages.
Overall and Lopez-Otin "Strategies for MMP inhibition in cancer: Innovations for the post-trial era," Nat Rev Cancer 2:657-672 (2002).
Palabrica et al., "Leukocyte accumulation promoting fibrin deposition is mediated in vivo by P-selectin on adherent platelets," Nature., 359(6398):848-851, Oct. 29, 1992.
Phillipson et al., "The neutrophil in vascular inflammation," Nat Med., 17(11):1381-1390, Nov. 7, 2011.
Raeber et al. "Molecularly engineered PEG hydrogels: a novel model system for proteolytically mediated cell migration," Biophysical Journal 89:1374-1388 (2005).
Rhee et al. "Microtubule function in fibroblast spreading is modulated according to the tension state of cell-matrix interactions," Proc Natl Acad Sci USA 104(13):5425-5430 (2007).
Sackmann et al., "Microfluidic kit-on-a-lid: a versatile platform for neutrophil chemotaxis assays," Blood., 120(14):e45-53, Epub Aug. 22, 2012.
Sahai "Illuminating the metastatic process," Nature Reviews Cancer 7:737-749 (2007).
Sahai and Marshall "Differing modes of tumour cell invasion have distinct requirements for Rho/ROCK signalling and extracellular proteolysis," Nat Cell Biol. 5(8):711-719 (2003).
Sahai et al. "Simultaneous imaging of GFP, CFP and collagen in tumors in vivo using multiphoton microscopy," BMC Biotechnology 5(14):1-9 (2005).
Savage et al. "Why does cytotoxic chemotherapy cure only some cancers?" Nat Clin Pract Oncol. 6:43-52 (2009).
Smith et al., "Interplay between shear stress and adhesion on neutrophil locomotion," Biophys J., 92(2):632-640, Epub Oct. 27, 2006.
Sporn, "The war on cancer," Lancet,1996, 347:1377-1381.
Sugarbaker et al. "Gastrectomy, peritonectomy, and perioperative intraperitoneal chemotherapy: the evolution of treatment strategies for advanced gastric cancer," Semin Surg Oncol. 21:233-248 (2003).
Tan et al. "Mechanisms of transcoelomic metastasis in ovarian cancer," Lancet Oncol. 7:925-934.
Tanos and Rodriguez-Boulan "The epithelial polarity program: machineries involved and their hijacking by cancer," Oncogene 27:6939-6957 (2008).
Todaro et al. "Initiation of Cell Division in a Contact-Inhibited Mammalian Cell Line," J. Cell. and Comp. Physiol. 66:325-333 (1965).
Vermeer et al. "Segregation of receptor and ligand regulates activation of epithelial growth factor receptor," Nature 422:322-326 (2003).
Wang et al. "Reciprocal interactions between beta1-integrin and epidermal growth factor receptor in three-dimensional basement membrane breast cultures: a different perspective in epithelial biology," Proc Natl Acad Sci USA. 95:14821-14826 (1998).
Warner et al., "Microfluidics-based capture of human neutrophils for expression analysis in blood and bronchoalveolar lavage," Lab Invest., 91(12):1787-1795, Epub Sep. 19, 2011.
Yamada and Cukierman "Modeling tissue morphogenesis and cancer in 3D," Cell 130:601-610(2007).
Yarrow et al. "A high-throughput cell migration assay using scratch wound healing, a comparison of image-based readout methods" BMC Biotechnology 4(21):1-9 (2004).
Zahm et al. "Cell migration and proliferation during the in vitro wound repair of the respiratory epithelium," Cell Motil. Cytoskeleton 37:33-43 (1997).
EP Extended European Search Report in European Application No. 17793545.9, dated Jul. 31, 2019, 9 pages.
Hamza and Irimia, "Whole blood human neutrophil trafficking in a microfluidic model of infection and inflammation," Lab on a Chip, May 2015, 15: 2625-2633.
Hoang et al., "Measuring neutrophil speed and directionality during chemotaxis, directly from a droplet of whole blood," Technology, Oct. 2013, 1: 49-57.
Partial Supplementary Search Report in European Application No. 17793545.9, dated Apr. 26, 2019, 11 pages.
EP Office Action in European Application No. 17793545.9, dated Nov. 3, 2020, 3 pages.

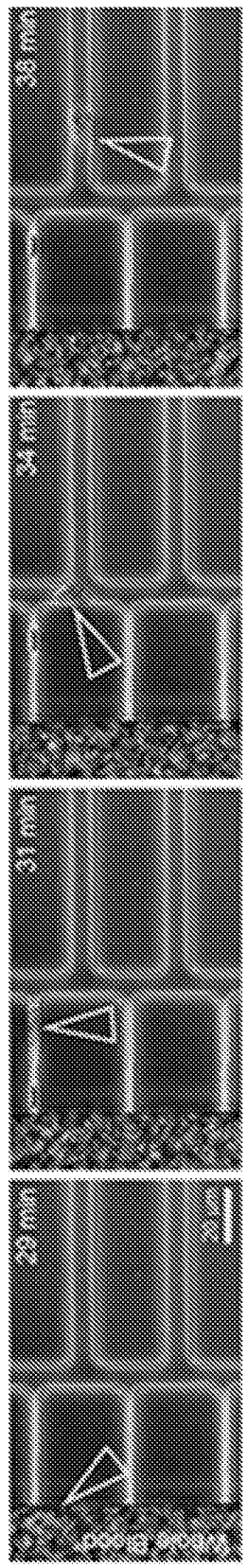

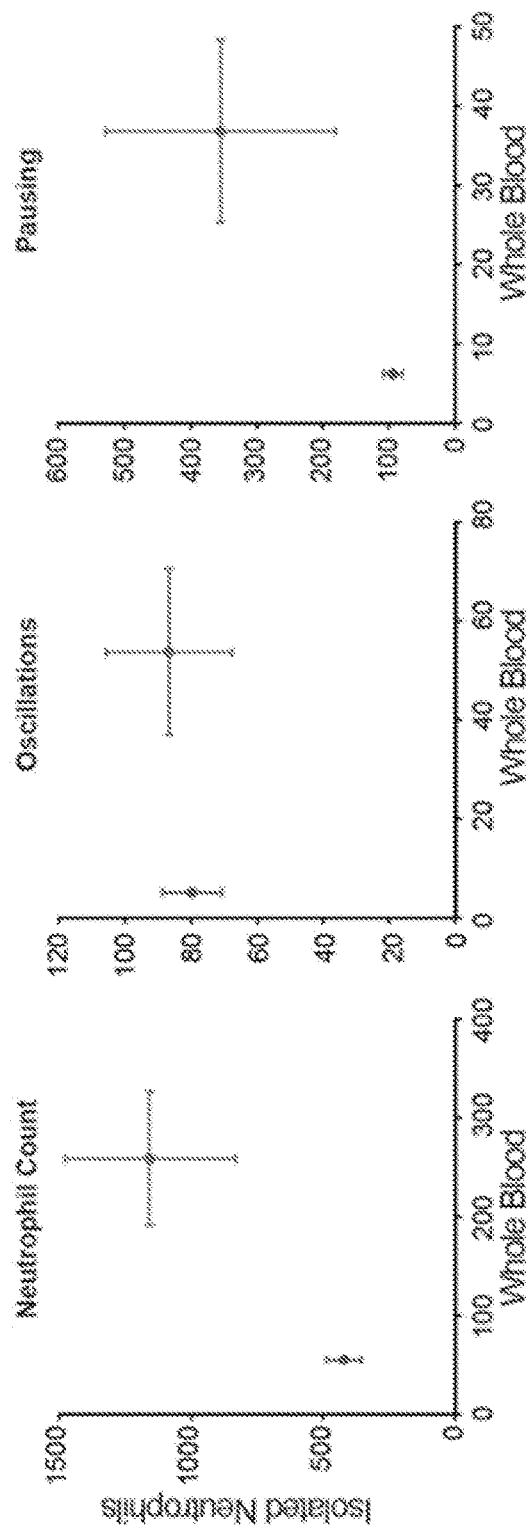
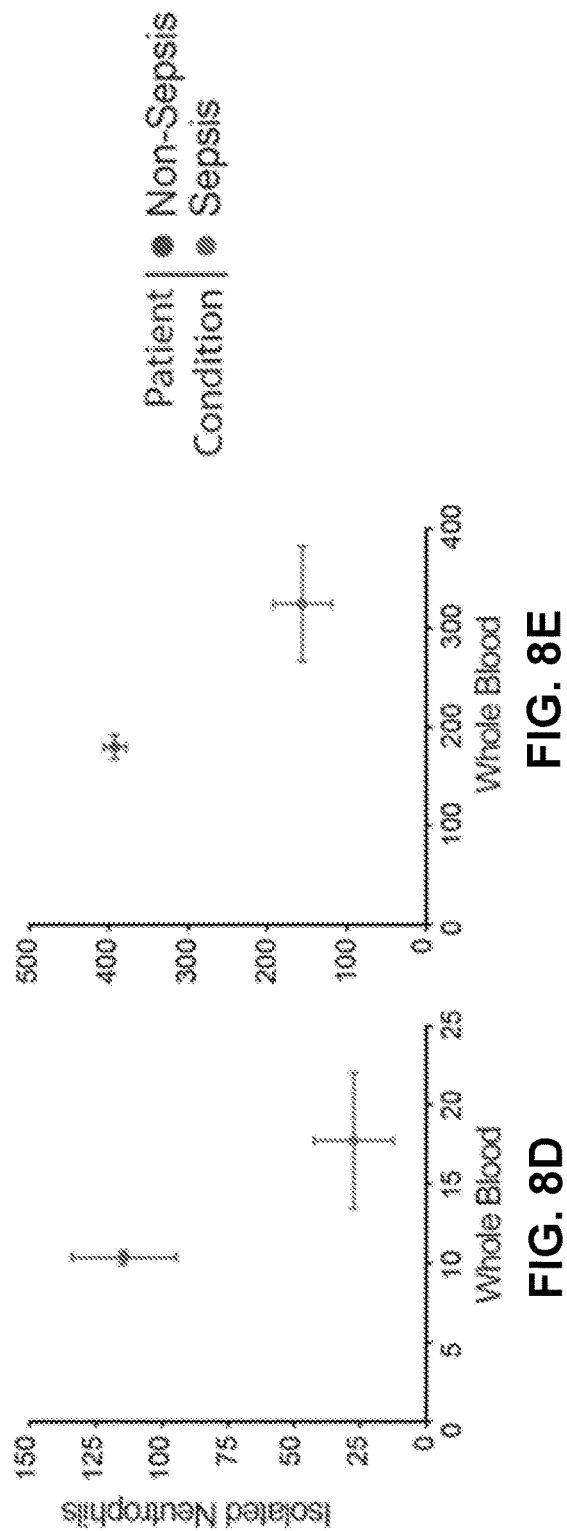

MICROFLUIDIC NEUTROPHIL ASSAYS AND SYSTEMS FOR DISEASE DETECTION

CROSS-REFERENCE TO RELATED APPLICATIONS

This application is a 371 U.S. National Phase Application of PCT/US2017/031557, filed on May 8, 2017, which claims the benefit of U.S. Provisional Application No. 62/332,659, filed on May 6, 2016 and U.S. Provisional Application No. 62/418,562, filed on Nov. 7, 2016, the contents of each of which are incorporated herein by reference in their entireties.

TECHNICAL FIELD

This invention relates to the detection of sepsis from whole blood samples.

BACKGROUND

Sepsis is caused by the body's response to infection which can lead to tissue damage, organ failure, and death. Sepsis can be difficult to diagnose and treat using current standards. As a result, sepsis is misdiagnosed in approximately 30% of patients, and is often treated after severe clinical symptoms have appeared. Microbiological cultures can help diagnose sepsis, but require two to three days to grow the bacterial cultures, thereby delaying treatment. Numerous biomarkers have been proposed for diagnosing sepsis, but no biomarkers are in clinical use at this time due to uncertainty about their specificity. Current epidemiological studies of sepsis recommend the use of classifications of end-organ-injury, such as the sequential organ failure assessment (SOFA) or quick SOFA (qSOFA) score, to diagnose sepsis. However, limitations in current diagnostics often delays sepsis treatment, resulting in longer hospital stays and worse outcomes for patients. In addition, current diagnostic and treatment approaches often lead to unnecessary prescription of antibiotics, which places a financial burden on both hospitals and patients, and promotes the propagation of antibiotic-resistant strains.

SUMMARY

The methods and microfluidic devices disclosed herein enable the investigation of cell motility in blood samples. In particular, the methods and devices provide a platform for monitoring the directionality, velocity, and migration persistence of neutrophils in the absence of an exogenous, i.e., externally added, chemical gradient, e.g., an added chemical attractant (e.g., chemoattractant), for the purposes of detecting and quantifying abnormal neutrophil motility phenotypes, using low sample volumes and with minimal, if any, activation of the neutrophils. This platform can be used to diagnose a particular disease or ailment in a subject, such as sepsis or Systemic Inflammatory Response Syndrome (SIRS) or SIRS-like disorders, or predict whether a subject is more likely to develop the particular disease or ailment. In particular, the devices and methods described herein provide the ability to analyze intrinsic neutrophil motility changes in the presence of factors in the blood, e.g., blood plasma, to enable highly specific and sensitive diagnosis of sepsis by quantifying particular neutrophil motility patterns directly in the blood of subjects that are suspected of having sepsis or developing sepsis, e.g., hospital patients who have or are at risk of developing an infection.

Machine learning algorithms were used to select a set of particular sepsis-specific motility signatures for monitoring and to establish a threshold quantitative score for these signatures indicative of sepsis, and the result enables sepsis to be diagnosed in critically ill patients with an accuracy of 97% or more. Thus, the present methods represent a significant performance improvement compared to current sepsis diagnostic capabilities. In addition, the devices and methods disclosed herein can be used to monitor the efficacy of sepsis treatment by assaying blood samples from a sepsis patient undergoing treatment over a period of time to quantify changes in neutrophil motility behavior, e.g., to determine whether neutrophils begin exhibiting a motility phenotype more similar to neutrophils form a healthy subject. Moreover, the devices and methods disclosed herein can be used to screen compounds for their potential uses as sepsis treatments, e.g., as new antibiotics or inflammation mediators.

In addition, use of the new devices is logistically simple and requires reduced processing time because separation techniques to isolate neutrophils are unnecessary and the devices do not rely on the use of introduced chemoattractant gradients. Instead, the devices can use a baffle filter and/or the size of migration channels to inhibit the movement of undesired cells from a whole blood sample applied directly to the device to a greater extent than the movement of desired motile cells such as neutrophils into the device. The neutrophils then intrinsically migrate over time from the sample and through the migration channels. The migration behaviors of the neutrophils can then be monitored in the migration channels and in the migration chamber of the device using time-lapse microscopy.

In a first general aspect, the subject matter disclosed herein is embodied in microfluidic devices that include a sample loading chamber with one or more outlets, a migration chamber having one or more inlets and configured and sized to provide motile cells a choice of directional migration, and one or more migration channels arranged in fluid communication between the one or more outlets of the sample loading chamber and the one or more inlets of the migration chamber, wherein each migration channel is connected to enable a sample to flow from an outlet of the sample loading chamber to an inlet of the migration chamber. The migration channels, e.g., inlet ends of the migrations channels, can be sized to allow the migration of neutrophils. In some implementations, the inlet ends of the migration channels can be sized to exclude red blood cells from entering the channels to a greater extent than neutrophils. In some embodiments, the microfluidic devices further include, e.g., are filled with, a buffer liquid that includes no exogenous chemical attractant.

The microfluidic devices can further include a baffle arranged in fluid communication between the one or more outlets of the sample loading chamber and the one or more migration channels or within the one or more migration channels, but at a point before each migration channel enters an inlet of the migration chamber. In some implementations, the baffle can have one or more passageways configured to inhibit the movement of red blood cells through the baffle to a greater extent than the baffle inhibits movement of the neutrophils through the baffle. The cross-sectional area of the baffle passageway normal to the sample transport path in the baffle passageway can be less than a red blood cell cross-sectional area, and wherein a width of the cross-sectional area is less than a red blood cell diameter. The microfluidic device can further include an exit channel in fluid communication with the migration channel at a point beyond the baffle and before the migration channel enters the inlet of the migration chamber.

In some implementations, the cross-sectional area of the migration channels or baffle passageways is greater than a red blood cell cross-sectional area, and wherein one or more migration channels or baffle passageways have at least one turn, such that red blood cells are prevented from moving past the turn.

In some implementations, the microfluidic devices include a plurality of baffle passageways, and a plurality of migration channels; wherein each baffle passageway is in fluid communication with a migration channel, and wherein the migration channels and the migration chamber each comprise a transparent cover material to enable motility of neutrophils to be monitored in the migration channels and the migration chamber. The microfluidic device can include a substrate, and the chambers and channels of the device are arranged in fluid communication on the substrate.

In another aspect, the subject matter of the disclosure is embodied in methods of monitoring the motility of blood cells, e.g., neutrophils, in a microfluidic device, for example, in a microfluidic device as described herein. The methods include adding a blood sample to a sample loading chamber of a microfluidic device that include one or more migration channels that each have a first end sized to permit neutrophils to enter the migration channels, wherein the microfluidic device is filled, e.g., primed, with a buffer liquid that includes no exogenous chemical attractant; and monitoring spontaneous motility of one or more neutrophils in the one or more migration channels in the absence of an exogenously added chemical attractant gradient. In these methods, a pattern of spontaneous motility of the one or more neutrophils in the blood sample that is different from a pattern of spontaneous motility of one or more neutrophils in a blood sample from a healthy person indicates that the blood sample is from a subject who has sepsis.

In various implementations of these methods, the devices can include a sample loading chamber with an outlet; a migration chamber having an inlet and configured to enable motile cells a choice of directional migration; and one or more migration channels arranged in fluid communication between the one or more outlets of the sample loading chamber and the one or more inlets of the migration chamber. The methods further include adding a blood sample to the sample loading chamber; incubating the device under conditions and for a time sufficient to enable movement of cells in the sample from the sample loading chamber into the one or more migration channels; and monitoring motility of neutrophils in the one or more migration channels and the migration chamber.

In some implementations, the motility of neutrophils can be monitored by quantifying one or more of the velocity, migration distance, migration direction, velocity persistence, and directional persistence of neutrophils in the one or more migration channels. In some cases, the motility of neutrophils can be monitored by determining the number of spontaneously migrating neutrophils. In some implementations, the motility of neutrophils can be monitored by quantifying two or more of the following neutrophil motility parameters: the number of spontaneously migrating neutrophils (N); the number of neutrophils that undergo a migratory oscillation (O); the number of neutrophils that undergo a migratory pause (P); whether neutrophils reverse their migration (R); the average distance migrated by neutrophils (AD); the maximum migration distance (MD); the mean velocity of neutrophils (V); the mean acceleration of neutrophils (A); the mean distance of oscillatory migration (OD); the mean forward migration of neutrophils away from the migration chamber entrance, e.g., a maze chamber (F); the mean vertical migration of neutrophils parallel to the migration channels (VM); the mean horizontal migration of neutrophils perpendicular to the migration channels (HM); and the mean nucleus size of migrating neutrophils (S). In some cases, the motility of neutrophils can be monitored by quantifying the following neutrophil motility parameters: the number of spontaneously migrating neutrophils (N); the number of neutrophils that undergo a migratory oscillation (O); the number of neutrophils that undergo a migratory pause (P); whether neutrophils reverse their migration (R); and the average distance migrated by neutrophils (AD).

In some implementations, a sepsis score can be determined by combining the quantified results for the neutrophil motility parameters; and wherein a sepsis score that is above a certain threshold indicates that the subject has sepsis or will develop sepsis. In some cases, a sepsis score is determined using the following formula:

$$\text{Sepsis Score} = \frac{N(O + P + R + AD)}{10^3},$$

wherein N is the number of spontaneously migrating neutrophils, O is the number of neutrophils that undergo a migratory oscillation, P is the number of neutrophils that undergo a migratory pause, R is the number of neutrophils that reverse migration, and AD is the average distance traveled by the neutrophils. In some implementations, a sepsis score of 30 and above indicates that the subject has sepsis or will develop sepsis In some implementations, the blood sample to be used for testing in the microfluidic device is collected from a human or animal subject, e.g., a mammal, e.g., a laboratory or domesticated mammal such as a monkey, dog, cat, rabbit, horse, cow, sheep, or goat.

In another aspect, the subject matter of the disclosure can be embodied in methods of diagnosing sepsis in a subject, in which the methods can include obtaining a device as described herein, adding a blood sample, e.g., a whole blood sample, a diluted whole blood sample, or a blood plasma sample, to the sample loading chamber; incubating the device under conditions and for a time sufficient to enable movement of cells in the sample from the sample loading chamber into the migration channel; monitoring the motility of one or more neutrophils in the migration channel and/or the migration chamber; and determining a sepsis score by combining the quantified results for the neutrophil motility parameters using the formula $$\text{Sepsis Score} = \frac{N(O + P + R + AD)}{10^3};$$

wherein a sepsis score that is 30 or above indicates that the subject has sepsis. In some cases, the motility of neutrophils can be monitored by quantifying the number of spontaneously migrating neutrophils; the number of neutrophils that undergo a migratory oscillation; the number of neutrophils that undergo a migratory pause; whether neutrophils reverse their migration; and the average distance migrated by neutrophils.

As used herein, "motility" means the ability of a motile cell to move itself, e.g., at a specific migration rate. Motile cells include neutrophils.

As used herein, "spontaneous neutrophil migration" or "spontaneous neutrophil motility" refers to the particular migration characteristics of neutrophils in the absence of a chemical attractant gradient, e.g., from a subject who has sepsis. Neutrophils in the blood of subjects with sepsis exhibit dysregulated migration relative to the neutrophils present in the blood of subjects without sepsis, e.g., healthy subjects or hospital patients without sepsis. Particular migration patterns or behaviors are observed in spontaneous neutrophil migration that alone, or in combination, are indicative of sepsis. For example, greater numbers of spontaneously migrating cells, increased oscillation during migration, pausing during migration, reverse migration, and increased average migration distances are indicative of sepsis are all parameters that can be used to diagnose sepsis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the description and drawings, and from the claims.

DESCRIPTION OF DRAWINGS

FIGS. 3A to 3D are a series of still images from a time-lapse movie showing neutrophils migrating through the baffle filter and into the device of FIGS. 2A-C, while red blood cells are blocked.

FIG. 8A to 8E are a series of plots comparing the results for whole blood and isolated neutrophil assays run in parallel for non-septic and septic patient samples wherein five neutrophil migration behaviors were monitored.

DETAILED DESCRIPTION

Figure 1A:
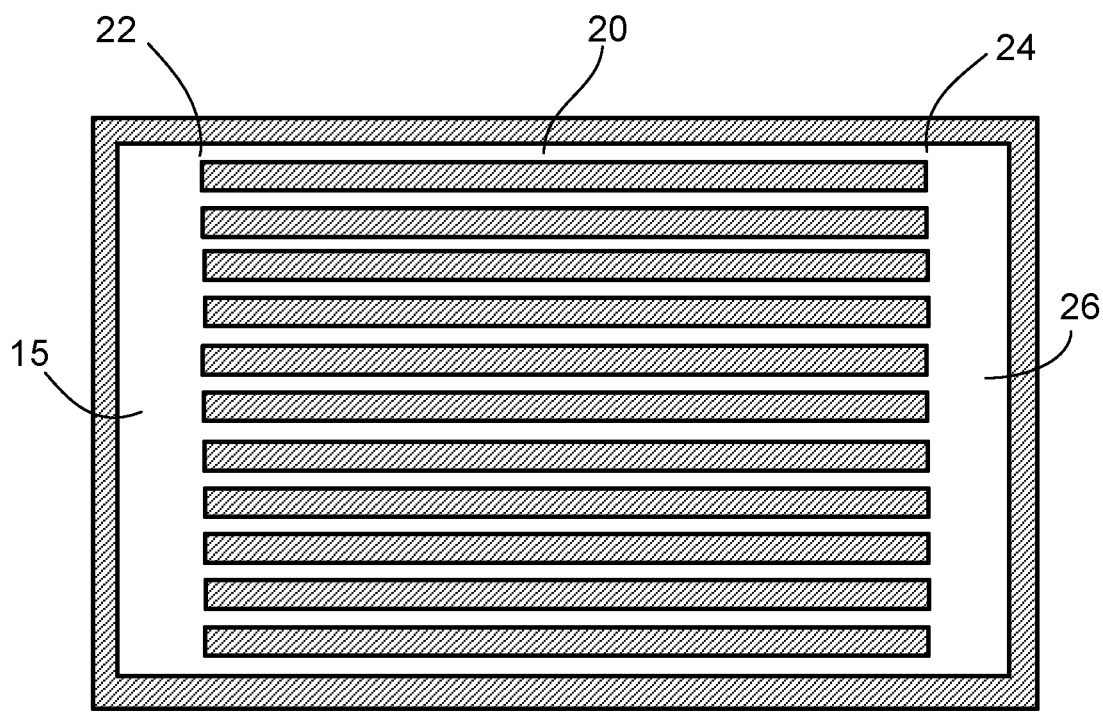
FIG. 1A is a schematic depicting an example of a microfluidic device as described herein, that includes a sample loading chamber and migration channels for monitoring cell motility.

The methods and devices disclosed herein provide microfluidic devices that can be used to investigate cell motility in blood samples for the purposes of detecting and quantifying abnormal motility phenotypes to determine the extent of damage to motile cells. Such information can be used to diagnose a particular disease or ailment, such as sepsis or Systemic Inflammatory Response Syndrome (SIRS) or SIRS-like disorders, or predict whether a patient is more likely to develop the particular disease or ailment. The devices disclosed herein provide a platform for diagnosing sepsis by analyzing the directional migration, velocity, and other migratory behaviors of neutrophils from the blood samples of patients with injuries that put them at high risk of having or developing sepsis.

Methods of Diagnosing Sepsis from Whole Blood Samples

The methods and devices disclosed herein provide new microfluidic devices that can be used to investigate cell motility, such as the motility of neutrophils in blood samples. The microfluidic devices can be used to monitor and measure the directional migration, speed, and other migratory behaviors of neutrophils in the absence of a chemical gradient, e.g., an added chemical gradient such as a chemoattractant, using low sample volumes and with minimal, if any, activation of the neutrophils. In particular, the methods can be used to measure and analyze the condition of cell motility of neutrophils in a subject that has suffered from an injury, trauma, or infection, so as to accurately determine whether the subject has sepsis. For example, the methods can be used to monitor spontaneous neutrophil motility in a blood sample, e.g., a whole blood sample, of a subject suspected of having sepsis, thereby enabling the diagnosis of sepsis in the subject.

The methods disclosed herein enable the measurement of patterns of neutrophil spontaneous motility in the microfluidic device directly from a droplet of blood, thereby preserving the physiological and biochemical environment of the neutrophils. Neutrophils are sensitive to circulating factors and integrate these signals to modulate their activation state and behavior. Neutrophil activation during sepsis is likely the cumulative effect of inflammation- and infection-related factors present in the circulation. Measuring neutrophil behavior directly from whole blood samples can amplify sepsis-specific behavioral changes in motility. Thus, the use of whole blood in the assay preserves the distinct neutrophil motility patterns that differentiate sepsis patients from subjects without sepsis. These distinct, sepsis-specific motility patterns would otherwise be compromised if the neutrophils were first isolated from the blood and then applied to the device in the absence of plasma factors.

Blood can be collected from a venous source or by a finger prick from a subject using standard methods. For example, venous blood is collected into Heparin-coated vacuum tubes. A small volume of the blood (100-500 μl) is then diluted 1:1 in a buffer, such as Iscove's Modified Dulbecco's Medium (IMDM)+20% FBS, and stained with a stain that to facilitate tracking of the cells, e.g., Hoechst stain, e.g., for a sufficient time, e.g., 15 minutes, prior to loading the diluted blood into the sample loading chamber of the device. In another example, the sample area of a subject's finger from which blood is to be drawn, usually the edge of the fingertip fat pad, is wiped thoroughly with an alcohol wipe and allowed to dry. A pressure-activated spring-loaded pricking device is then applied to the finger until activated. A droplet of blood will begin to form at the site, which is removed with a gauze wipe. A 20-50 μl sample is taken from the second droplet of blood and diluted, e.g., 1:1 in IMDM+20% FBS. This sample is then stained with Hoechst for at least 15 minutes prior to loading into the sample loading chamber of the device. Regardless of how the blood is collected, the blood should be tested within the first 3 hours after collection, because neutrophil activity declines as the blood ages.

The microfluidic devices disclosed herein are designed to have channels and mazes that enable direct observation of the motility patterns of neutrophils that migrate into the device from whole blood samples applied to the device, e.g., blood samples collected from healthy donors or subjects with sepsis.

Neutrophils exhibit a sepsis-specific spontaneous motility signature in straight microfluidic channels without the use of added chemo-attractants, which is highly correlated with sepsis in patients, whether they are present in whole blood or isolated ex vivo from the blood. However, assays using the devices disclosed herein enable higher precision measurements of neutrophil motility by incorporating narrow, branching microfluidic channels and mazes. This enables more precise identification and measurement of particular neutrophil motility patterns compared to straight microfluidic channels or more traditional cell migration assays that do not incorporate microfluidic channels, e.g., migration assays that allow cells to migrate over relatively larger surfaces such that it is difficult to measure and categorize the small, continuous directional changes made by the cells. Confining moving neutrophils to channels and mazes enables motility measurements that are less sensitive to signal noise.

Figure 1B:
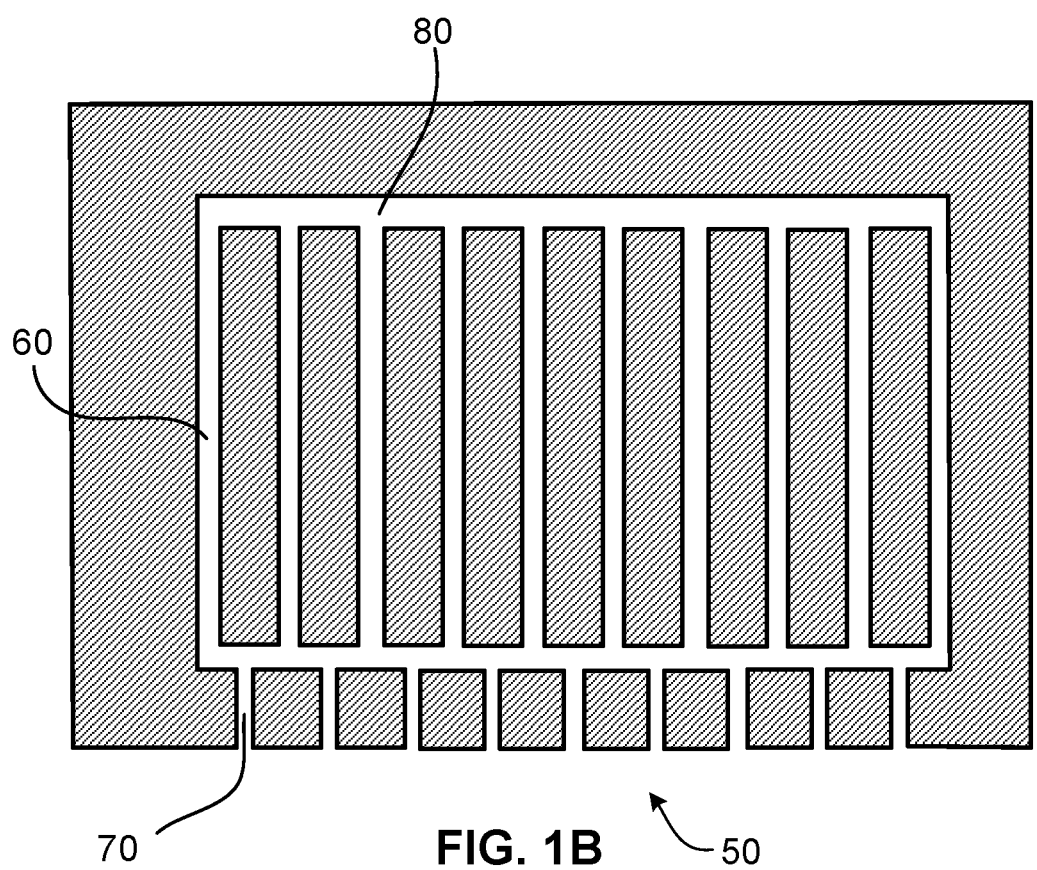
FIG. 1B is a schematic depicting an example of a microfluidic device as described herein, that includes a sample loading chamber, a baffle filter, and migration channels for monitoring cell motility.

FIG. 1A is a schematic of an example of a microfluidic device disclosed herein that can be used to monitor cell motility. The device integrates a sample loading chamber 15 into which a small volume of blood may be loaded, e.g., ~1 to 5 μL, a migration chamber 26, and a series of migration channels 20, each having an inlet 22 and an outlet 24, which are in fluid communication with the sample loading chamber 15 via their inlets 22 and with the migration chamber 26 via their outlets. These migration channels are used to detect and measure the directional choices, velocity, and migration persistence of motile cells. Thus, these channels must have a cross-sectional size selected or configured to enable the cells, e.g., neutrophils, to enter the channels while having sufficient contact with the inner walls to enable the neutrophils to move along the channels. In addition, the migration channels should be sized to prevent RBCs from entering. FIG. 1B is a schematic of another microfluidic device disclosed here that can be used to monitor cell motility. The device includes a sample loading chamber 50 into which a small volume of blood may be loaded, a migration channel 80, at least one migration channel 60, and at least one baffle passageway 70 that is in fluid communication with the sample loading chamber and the migration channel 60, such that a motile cell in a fluid sample deposited in the sample loading chamber can move through the baffle filter passageway 70 and into the migration channel 60. At least one migration channel is in fluid communication with the migration chamber.

In particular, for separating RBCs and undesired leukocytes from neutrophils in a human blood sample in the devices described herein, the height of the migration channels should be about 3-12 microns, e.g., 3-10 or 3-6 microns. Additionally, the width of the migration channel should be between about 3 and 12 microns, e.g., 3-10, 3-6, or 3.5-5.5 microns. With such dimensions, there is still room for the neutrophils to migrate past the RBCs and other leukocytes. Furthermore, the width prevents complete clogging of the migration channel by the RBCs and other leukocytes. If the channel cross-section is too small (e.g., less than 1 μm), gaps do not form between the RBCs and other WBCs to provide neutrophils with enough room, even after deforming their shape, to pass through.

The cross-sectional area of the migration channel can be smaller or larger than those described here, and can be used to analyze the migration of cells other than neutrophils including, for example, lymphocytes, monocytes, natural killer lymphocytes, platelets and megakaryocytes, epithelial cells, endothelial cells, cancer cells, bacteria, sperm, and the like. Table 1 provides a list of different examples of motile blood cells, their typical concentration in human blood, and an appropriate cross-sectional area of a rectangular shaped channel for allowing migration of the motile cells. Table 1 also lists channel cross-sectional areas for other motile cells such as bacteria, parasites and sperm cells. The device can also be used with cells from blood of other animals, e.g., murine, rabbit, monkey, or canine blood, as well. However, the dimensions of the migration channel 120 should be modified to accommodate the different sizes of cells obtained from these other types of blood. For example, neutrophils and RBCs from murine blood are smaller than those of humans (murine RBC are about 5-6 μm in diameter which humans are about 7 μm, and murine neutrophils cell diameter ranges 5-6 μm while human neutrophil cell diameter ranges 7-8 μm).

TABLE 1

| Blood Cell Type | Cells/μL blood - healthy individual | Typical channel size for migration |
| --- | --- | --- |
| Neutrophil (granulocyte) | 5,000 | 6 × 6 μm$^2$ |
| Eosinophil | 10 | 6 × 6 μm$^2$ |
| Monocyte | 50 | 10 × 10 μm$^2$ |
| Lymphocyte | 3,000 | 8 × 8 μm$^2$ |
| Dendritic Cell | 1 | 10 × 10 μm$^2$ |
| Circulating endothelial cell | 0.1 | 10 × 10 μm$^2$ |
| Fibrocyte | 0.1 | 6 × 6 μm$^2$ |
| Mast cell | 0.1 | 6 × 6 μm$^2$ |
| Circulating tumor cell | 0.01-1 | 10 × 10 μm$^2$ |
| Platelets | 50,000 | 2 × 2 μm$^2$ |
| Other motile cells in complex mixtures | | |
| Bacteria | | 1 × 1 μm$^2$ |
| Parasites (sporozoite phase) | | 5 × 5 μm$^2$ |
| Sperm cells | | 2 × 2 μm$^2$ |

In some implementations, a baffle filter 25 may be added to the device to further inhibit red blood cells (RBCs) from entering the migration channels 20, wherein the baffle filter 25 is in fluid communication with an outlet 17 of the sample loading chamber 15 and is also in fluid communication with the inlets 22 of the migration channels 20. The system can also include a connecting channel 35, that fluidly connects each of the outlets 24 of the migration channels 20.

The methods and devices disclosed herein are designed to detect and measure the sepsis-specific spontaneous motility signatures. More specifically, the methods and devices detect and measure one or more of thirteen distinct neutrophil spontaneous migration parameters in the migration channels 120 and the migration chamber 135 of the microfluidic device. Specifically, as provided in Table 1, the assay can detect (1) the number of spontaneously migrating neutrophils (herein abbreviated as an "N"); (2) the number of neutrophils that undergo a migratory oscillation (herein abbreviated as "O"); (3) the number of neutrophils that undergo a migratory pause (herein abbreviated as "P"); (4) whether neutrophils reverse their migration (herein abbreviated as "R"); (5) the average distance migrated by neutrophils (herein abbreviated as "AD"); (6) the maximum migration distance (herein abbreviated as "MD"); (7) the mean velocity of neutrophils (herein abbreviated as "V"); (8) the mean acceleration of neutrophils (herein abbreviated as "A"); (9) the mean distance of oscillatory migration (herein abbreviated as "OD"); (10) the mean forward migration of neutrophils away from the migration chamber, e.g., a maze chamber, entrance (herein abbreviated as "F"), (11) the mean vertical migration of neutrophils parallel to the migration channels 120 (herein abbreviated as "VM"); (12) the mean horizontal migration of neutrophils perpendicular to the migration channels 120 (herein abbreviated as "HM"); and (13) the mean nucleus size of migrating neutrophils (herein abbreviated as "S").

TABLE 2

| Neutrophil migration Parameter | Abbreviation | Definition |
| --- | --- | --- |
| 1. Spontaneously Migrating Neutrophil Count | N | The total number of neutrophils that migrate from the whole blood loading channel into the maze |
| 2. Oscillations | O | The total number of cells that switch direction twice in a channel and migrate for more than 15 um in each segment |
| 3. Mean and variance Pausing | P | The total number of cells that migrate less than 5 um for more than three frames |
| 4. Mean and variance Reverse Migration | R | The average migration distance of neutrophils towards the maze entrance [μm] |
| 5. Average Distance Migrated | AD | The average migration distance of neutrophils in the mazes [μm] |
| 6. Maximum migration Length | MD | The maximum migration distance of neutrophils in the linear portions of the mazes [μm] |
| 7. Mean and Variance of Velocity | V | The average velocity of neutrophils in the mazes [μm/min] |
| 8. Mean and Variance of Acceleration | A | The average acceleration of neutrophils in the mazes [μm/min] |
| 9. Mean Distance of Oscillatory migration | OD | The average migration distance of oscillating neutrophils [μm] |
| 10. Mean and Variance Forward migration | F | The average migration distance of neutrophils migrating away from the migration chamber, e.g., maze, entrance [μm] |
| 11. Mean and Variance Vertical migration Distance | VM | The average migration distance of neutrophils migrating parallel to the channels [μm] |
| 12. Mean and Variance Horizontal migration Distance | HM | The average migration distance of neutrophils migrating perpendicular to the channels [μm] |
| 13. Mean and Variance of Nucleus Size | S | The average nucleus size of migrating cells |

In some implementations, only one or two of the neutrophil migration parameters of Table 2 are measured in the migration channels 120 and the migration chamber 135 of the microfluidic device. In other implementations, three, four, five, six, seven, eight, nine, ten, eleven, twelve, or all thirteen of the neutrophil migration parameters of Table 2 are measured in the migration channels 120 and the migration chamber 135 of the microfluidic device.

In some implementations, any one of N, O, P, R, AD, MD, V, A, OD, F, VM, HM, or S is scored after adding a whole blood sample to the microfluidic device. In some implementations, N plus any one or more of O, P, R, AD, MD, V, A, OD, F, VM, HM and S are scored after adding a whole blood sample to the microfluidic device. In some implementations, O plus any one or more of N, P, R, AD, MD, V, A, OD, F, VM, HM and S are scored after adding a whole blood sample to the microfluidic device. In some implementations, P plus any one or more of N, O, R, AD, MD, V, A, OD, F, VM, HM, and S are scored after adding a whole blood sample to the microfluidic device. In some implementations, R plus any one or more of N, O, P, AD, MD, V, A, OD, F, VM, HM, and S are scored after adding a whole blood sample to the microfluidic device. In some implementations, AD plus any one or more of N, O, P, R, MD, V, A, OD, F, VM, HM, and S are scored after adding a whole blood sample to the microfluidic device. In some implementations, MD plus any one or more of N, O, P, R, AD, V, A, OD, F, VM, HM, and S are scored after adding a whole blood sample to the microfluidic device. In some implementations, V plus any one or more of N, O, P, R, AD, MD, A, OD, F, VM, HM, and S are scored after adding a whole blood sample to the microfluidic device. In some implementations, A plus any one or more of N, O, P, R, AD, MD, V, OD, F, VM, HM, and S are scored after adding a whole blood sample to the microfluidic device. In some implementations, OD plus any one or more of N, O, P, R, AD, MD, V, A, F, VM, HM, and S are scored after adding a whole blood sample to the microfluidic device. In some implementations, F plus any one or more of N, O, P, R, AD, MD, V, A, OD, VM, HM, and S are scored after adding a whole blood sample to the microfluidic device. In some implementations, VM plus any one or more of N, O, P, R, AD, MD, V, A, OD, F, HM, and S are scored after adding a whole blood sample to the microfluidic device. In some implementations, HM plus any one or more of N, O, P, R, AD, MD, V, A, OD, F, VM, and S are scored after adding a whole blood sample to the microfluidic device. In some implementations, S plus any one or more of N, O, P, R, AD, MD, V, A, OD, F, VM, and HM are scored after adding a whole blood sample to the microfluidic device.

For example, in some implementations, any two, three, four, five, six, seven, eight, nine, ten, eleven, twelve, or all thirteen of N, O, P, R, AD, MD, V, A, OD, F, VM, HM and S are scored after adding a whole blood sample to the microfluidic device.

In some implementations, the number of spontaneously migrating neutrophils (the "N" migration parameter); the number of migratory oscillation events ("O" migration parameter); the number of migratory pausing events (the "P" migration parameter); the number of reverse migration events (the "R" migration parameter); and the average distance by which the neutrophils travel (the "AD" migration parameter) are scored after adding a whole blood sample to the microfluidic device.

Figures 4A, 4B, 4C:
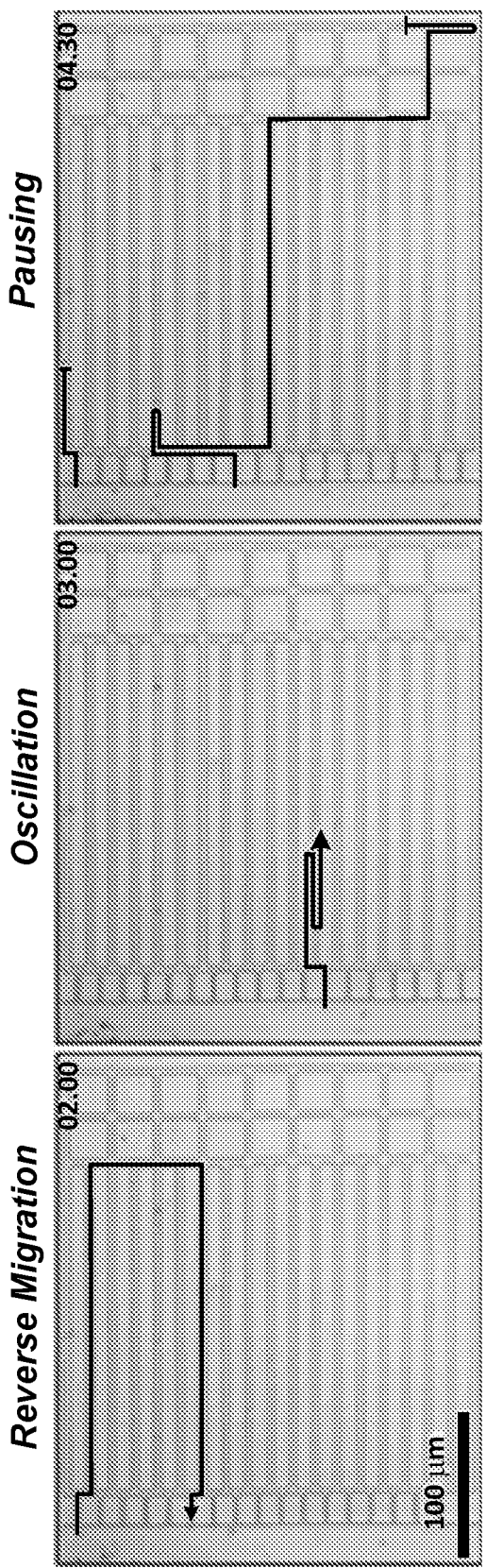
FIGS. 4A-4C are a series of still images from a time-lapse movie showing an example of several different spontaneous migration behaviors by neutrophils from a septic patient blood sample, including reverse migration (4A), oscillation (4B), and pausing (4C).

FIGS. 4A-4C provide a series of still images from a time lapse movie showing examples of spontaneous migration behaviors exhibited by neutrophils present in a sample collected from a sepsis patient. The track lines in the panels of FIGS. 4A-4C show examples of reverse migration (4A), oscillation (4B), and pausing (4C) by neutrophils in the migration channels and migration chamber of the device.

Microfluidic Devices for Detecting Sepsis and SIRS

The microfluidic devices disclosed herein can be used to monitor the native motility of neutrophils in a blood sample from a subject, and, in particular, identify and monitor the spontaneous migration of neutrophils into and within a space within the device without the use of a chemical gradient, e.g., an added chemoattractant, to attract the neutrophils into the space. The space within the device is selected and configured to have a dimension and length that allows the neutrophils to move freely in more than one direction at any given time. Neutrophils from blood enter such migration spaces within the device in migration channels that are sized to allow the passage of neutrophils into the lumens of the migration channels while excluding other cells types from the space. Once inside the channel lumens, the migratory behaviors of the neutrophils, e.g., the directional motility, speed, and other migratory behaviors, are observed and analyzed.

Figure 2A:
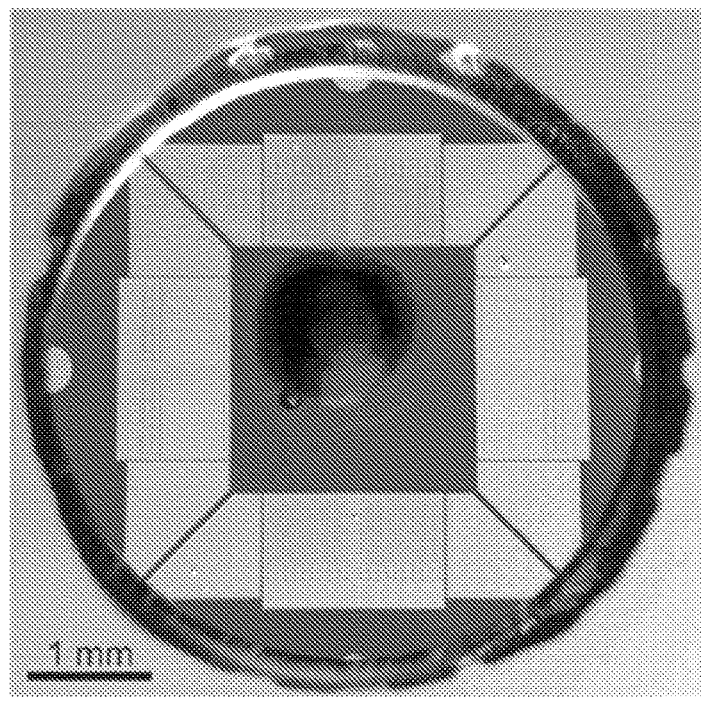
FIG. 2A is a macroscopic image of an example of a microfluidic device as described herein.
Figure 2B:
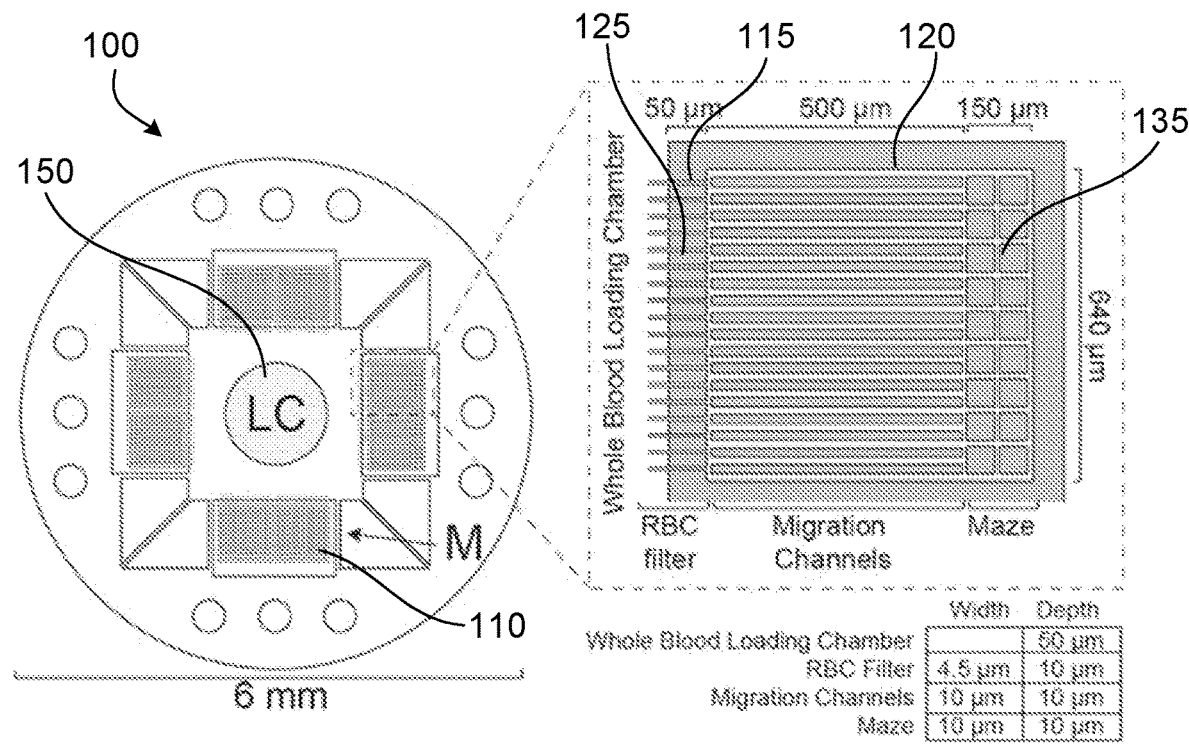
FIG. 2B is a schematic depicting the components of the device of FIG. 2A, including the whole blood loading chamber (LC) and the migration blocks (M), and an enlarged image of one of eight migration blocks which includes a baffle filter, migration channels, and a migration chamber. The indicated measurements are useful examples, but do not limit the scope of the disclosure and inventions described herein.

FIG. 2A provides a macroscopic image of an example of a microfluidic device for analyzing cell motility, e.g., neutrophil motility. FIG. 2B is a schematic example of the microfluidic device 100 and including a close up view of a portion of the device 100. The microfluidic device can be used for monitoring the migratory behaviors of motile cells. The device 100 integrates several features, including a deeper central sample loading chamber 150 into which a small volume of blood (~1 to 5 µL) is loaded; a baffle filter 125, which limits entry of red blood cells (RBCs) into the channels of the assay field; and shallower migration channels 120 and a geometrical migration chamber 135 to detect and measure the directional choices (e.g., reverse migrations and oscillations), velocity, and migration persistence, e.g., persistence of direction and velocity, with high precision. The sample loading chamber 150 receives a fluid sample, where the fluid sample can contain multiple motile cells and non-motile cells. For example, the fluid sample could be a droplet of whole blood that contains both neutrophils and red blood cells (RBCs). As shown in the example of FIG. 2B, the sample loading chamber 150 is surrounded by at least one migration block 110, into which a motile cell can migrate. Each migration block 110 is composed of at least one baffle filter 125 made up of at least one baffle passageway 115, at least one migration chamber 135, and at least one migration channel 120. Each migration chamber 135 of the chamber block 110 is fluidly coupled to the sample loading chamber 150 through at least one baffle filter 125 and a at least one migration channel 120.

As shown in FIG. 2B, the baffle filter 125 is arranged in fluid communication between an outlet of the sample loading chamber 150 and the migration channel 120, such that a fluid sample deposited in the sample loading chamber can move through the baffle filter 125 into the migration channel 120. The migration channel 120 is arranged in fluid communication between an outlet of the baffle filter 125 and an inlet of the migration chamber 135.

In the present example, the sample loading chamber 150 has a circular profile, though other shapes can also be used. The diameter of the sample loading chamber 150 can be between about 10 microns to about 2000 microns. For example, the diameters can be about 10, 20, 30, 40, 50, 60, 70, 80, 90, 100, 150, 200, 250, 300, 350, 400, 450, 500, 750, 1000, or 2000 microns. If the diameter is too large, it will increase the time required for the motile cells, e.g., neutrophils, far from the baffle 125 to exit the sample loading chamber and enter the next part of the device.

The sample loading chamber 150 can have a volume in the range of about 0.5 microliters to about 20 microliters. For example, the sample loading chamber 150 can have a volume of about 1, 2, 3, 4, 5, 7, 8, 10, 12, 15, 18, or 20 microliters.

The migration chamber disclosed herein is designed to enable motile cells to migrate in one of at least two or more different directions at any given time, e.g., in two directions, in three directions, or in four directions. The migration chamber can be one larger chamber that allows the free movement of motile cells. In some implementations, the migration chamber can be arranged into a maze, wherein the chamber is subdivided into two or more smaller chambers separated by barriers, e.g., substrate barriers, or can be arranged into numerous passageways that are separated from each other by barriers or walls. In the present example, the migration chamber 135 is arranged into a maze chamber wherein the chamber is subdivided by barriers into intersecting passageways that are arranged as a grid, but one of skill in the art would understand that the passageways in the maze chamber can be arranged in any pattern as long as the motile cells can migrate in one of at least two different directions at any given time. The migration chamber 135 has a square shaped profile in the present embodiment, but other shapes can also be used. The migration chamber 135 should be sized to allow the desired motile cells to pass through it freely. The migration chamber can be between about 10-2000 microns wide, 50-2000 microns long, and 10-500 microns deep. For example, the width can be 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, 1000, or 2000 microns. The length can be 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, 1000, or 2000 microns. The depth can be 10, 20, 30, 40, 50, 60, 70, 80, 90, 100, 110, 120, 130, 140, 150, 160, 170, 180, 190, 200, 250, 300, 350, 400, 450, or 500 microns.

During operation of the device, the sample loading chamber 150 is filled with the fluid sample. Cells within the fluid sample begin moving toward the openings of the baffle filter(s) 125. Cell movement does not occur based on external pressure source (e.g., introducing pressure differences using syringe pumps or liquid pumps) or any flow of the liquid within the device. Instead, cell movement through the fluid in the device is the result of a combination of passive factors, including a static pressure difference created by filling the sample loading chamber with the fluid sample, natural diffusion, and/or random Brownian motion, and the motion of motile cells (e.g., by "crawling" in the case of neutrophils or swimming for other motile cells such as certain bacteria and sperm) towards the baffle filter(s) 125. Cell movement in the fluid sample is not based on the presence of an added attractant gradient in the device, e.g., a chemoattractant.

To help prevent undesired cells from inhibiting or interfering with the active migration of motile cells, the baffle filter 125 is configured to inhibit the movement of undesired cells to a greater extent than the desired motile cells. For example, in the device shown in FIG. 2B, the baffle filter 125 includes one or more passageways 115 sized to selectively allow migration of the desired motile cells, while being small enough to substantially block the movement of other undesired motile and non-motile cells into the migration channel 120. For instance, for neutrophil analysis in a whole blood sample, the dimensions of the passageways are sized to allow migration of neutrophils in the blood sample, while being small enough to substantially impede the passage of other cells in the sample, such as RBCs and other leukocytes (e.g., monocytes and lymphocytes). While neutrophils are generally the same size or larger than RBCs and other leukocytes (e.g., a typical human neutrophil is between about 8-15 microns in diameter; typical human lymphocytes and monocytes have diameters of about 7 microns and between about 10-30 microns, respectively; a typical disc-shaped human RBC has a diameter between about 6-8 microns and a height between about 2-2.5 microns), neutrophils are more deformable in shape than RBCs and other blood cells, and thus can change dimensions to migrate through tight passages that would otherwise impede the movement of other leukocytes and RBCs.

FIGS. 3A-D depict a series of still images from a time-lapse movie showing that after the blood droplet is pipetted into the central sample loading chamber, the neutrophils spontaneously migrate through the RBC filter and into the migration channels and migration chamber, while the RBCs are excluded from entering the migration channels. Time-lapse imaging of the migration channels and migration chambers is used to measure neutrophil behavior over a period of time, e.g., 4 or more hours.

One way of appropriately sizing the baffle passageways 115 to allow neutrophils, but not other cells to pass through, is to restrict the cross-sectional area of the passageway along a plane normal to the direction of cell movement. In one example, one could use microfluidic channels having cross sections smaller than that of the undesired cells. However, such channels could be completely obstructed at their entrance by a collection of cells, precluding the formation of gradients. Furthermore, cross-sectional areas that are smaller than that of the undesired cells could also impede the desired motile cell migration, because such cells would have no gaps to pass through.

Thus, in another example of the microfluidic devices disclosed herein, the cross-sectional areas of the passageways 115 and/or of the migration channels 120 are configured to be larger than the largest diameter or cross-sectional dimension of one or more of the different undesired cells. At the same time, a first dimension of the passageway 115 and/or migration channel 120 cross-section is configured to be about equal to or less than a size of the undesired cell. With this configuration, substantial movement of the undesired cell(s) through the passageway 115 would still be restricted, but the desired motile cell (e.g., neutrophil) modifies its shape as it enters the passageway 115 so as to migrate around and between the undesired cells through open gaps in the passageway 115. The desired motile cells thus "squeeze" their way around and between the undesired cells. As an example, a first dimension of the cross-section (e.g., width) can be set larger than the cell(s) to be blocked, whereas a second dimension of the cross-section (e.g., height) is set to be smaller than the cell(s) to be blocked.

The movement of undesired cells relative to the movement of desired motile cells also can also be restricted by adding a relatively sharp turn in the baffle passageway 115 or migration channel 120, e.g., a turn of at least about 90 degrees. Such a turn creates congestion/gridlock in the movement of undesired cells. In particular, as a cell moves, tumbles, floats, or is pushed into the corner, it tends to block the advance of other trailing cells behind it by restricting the cross-section of the channel to less than the diameter of a single cell. This configuration works well for cells that move based on granular flow (e.g., RBCs), because the granular flow force pushing the cells in the channel is not enough to deform the cells through the restricted section. However, since the cross-section of the channel is larger than that of the undesired cell, gaps still exist for the desired motile cells to pass through. Both the baffle filter 125 and the migration channel 120 are sized to allow the desired motile cell to pass from the sample loading chamber 150 to the migration chamber 135.

The baffle filter 125 can include a single passageway 115 or multiple passageways 115, each of which is in fluid communication with the inlet of a migration channel 120 and each of which is configured to inhibit movement of undesired cells as described above. For example, as shown in FIG. 2B, the baffle filter 125 includes several passageways 115 that together create a comb-like structure. The baffle filter 125 can include, but is not limited to, between 1 and 50 passageways, e.g., 15, 16, 17, 18, 19, or 20 passageways. The lengths (i.e., the distance along the direction of cell movement into the migration channel 120) can be in the range of between about 10 to about 100 microns. For example, the length can be between about 20 to about 80 microns, between about 30 to about 70 microns, or between about 40 to about 60 microns. In some embodiments, the length is 50 microns.

Once the desired motile cells have migrated away from the fluid sample in the sample loading chamber 150 and passed through the baffle passageways 108, the motile cells enter the migration channel 120. The migration channel 120 should be sized to allow at least the desired cells to pass, e.g., "squeeze," through. For example, the height of the migration channel 120 can be between about 8 and 20 microns, though larger heights also can be used. The lengths (distance along the direction of migration) of the migration channel 120 can be between about 10-2000 microns, e.g., 75 microns long. The widths of the migration channel 120 can be between about 8-12 microns, though other widths can also be used.

One or more migration channels 120 are in fluid communication at one end with the baffle filter 125 through one or more baffle passageways 115, and are in fluid communication at the other end with one or more migration chambers 135. The migration block 110 can include, but is not limited to, between 1 and 100 migration channels 120 that join the baffle filter 125 to the migration chamber 135, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 migration channels 120. The migration channels 120 can run directly and along the shortest distance from the baffle filter 125 to the migration chamber 135. Alternatively, the migration channels 120 can run along a more indirect route between the baffle filter 125 and the migration chamber 135, e.g., any indirect route between the baffle filter 125 and migration chamber 135 that fits physically within the confines of the migration block 110. For example, as shown in FIG. 2B, the example device includes several migration channels 120 that run parallel to each other directly from the baffle filter 125 to the migration chamber 135.

Device Fabrication, Assay Preparation, and Use

The microfluidic devices described herein can be manufactured using various methods. In one example, devices described herein are fabricated using standard photolithography or soft lithography techniques to generate a silicon wafer, which is used as a negative mold to generate polydimethylsiloxane (PDMS) devices. For example, the mold can be formed by applying and sequentially patterning two layers of photoresist (e.g., SU8, Microchem, Newton, Mass.) on a silicon wafer using two photolithography masks according to known methods. The masks can contain features that define the different aspects of the device 100 such as the input chamber, the baffle, the migration channels, and the connecting channel/migration chamber.

The wafer with the patterned photoresist then can be used as a master mold to form the microfluidic parts. A PDMS (e.g., Fisher Scientific, Fair Lawn, N.J.) solution then is applied to the master mold and cured. After curing, the PDMS layer solidifies and can be peeled off the master mold. The solidified PDMS layer includes grooves and/or recesses corresponding to the passageways, migration channels, and migration chamber of the device 100. In some implementations, the mold pattern is designed to include the features of multiple devices 100.

Each device can be cut out from the PDMS layer using, for example, a hole puncher (e.g., a 5 mm hole puncher). Similarly, the sample loading chamber also can be formed by using a smaller hole puncher (e.g., a 1.2 mm diameter hole puncher) to punch out PDMS material from the PDMS layer. The PDMS devices then are bonded to a substrate such as a glass slide or multi-well plate (i.e., each device is positioned in a corresponding well of the well plate) (e.g., Mattek, Ashland, Mass.). For example, a bottom surface of the PDMS devices can be plasma treated to enhance the bonding properties of the PDMS. The plasma treated PDMS devices then are placed on the glass slide or into the bottom of a well on a plate and heated to induce bonding. The microfluidic channels of the device can also be exposed to plasma treatment prior to bonding to render the channels hydrophilic. FIG. 1 and FIG. 2B are schematics depicting examples of microfluidic device fabricated according to the foregoing procedures.

The example of a microfluidic device 100 described above, includes a substrate layer of glass and a top layer of PDMS in which the sample loading chamber 150, the baffle filter 125, the migration channel 120 and the migration chamber 135 are formed. In other implementations, both the substrate layer and the top layer can be PDMS substrates or other similar materials such as, e.g., plastic, glass or silicone.

In general, the top layer (or the bottom layer) in which the baffle filter 125, migration channel 120, and migration chamber 135 are formed should be selected to have the following characteristics. The layer can be gas-permeable so that air in the baffle filter 125, migration channel 120, and migration chamber 135 can be displaced through the layer, either by pumping fluid into the device and/or by placing the device under vacuum, so that air can be removed from the device, e.g., from the migration channels and migration chamber, and filled with an appropriate priming solution before a sample, e.g., a blood sample or diluted blood sample, is introduced into the loading chamber. Furthermore, the layer can be transparent so as to facilitate image capture of cell motility within the device.

For example, the device can be placed under a vacuum. The vacuum causes any air present in the channels or chambers to diffuse through the gas-permeable material of the top layer (e.g., the PDMS layer). This process removes air bubbles that would otherwise be present in the fluidic channels of the device, and which could potentially block the passage of cells through the baffle filter 125 and migration channel 120. To establish the vacuum, the device can be placed into a desiccator, in which air pressure is reduced to a vacuum level of about 17-25 inches of water, for at least about 15 minutes.

In one example, the device 100 is primed prior to starting the assay to allow time for degassing. In some implementations, the device 100 is primed at least 5 minutes prior adding blood to the sample loading chamber of the device to begin the assay. In some implementations, the device is primed 5, 10, 15, 20, 25, 30, 35, 40, 45, 50, 55, 60, 75, 100, 115, 130, 145, or 160 minutes before adding the blood. In some implementations, the device is primed 1, 2, 3, 4, 5, 6, 7, 8, 9, 10, 11, or 12 or more hours before adding the blood. In one example, device priming begins with the addition of a priming solution into the sample loading chamber and around the outside of the device 100, e.g., addition of IMDM+10% FBS+10% Fibronectin, physiologic serum (0.9% NaCl), plasma, plasma isolated from the same patient blood sample, IMDM+0.5% human serum albumin (HSA), Hanks buffer+0.5% HSA, or any other solution suitable for neutrophils to migrate. The device 100 is then placed in a vacuum, and then allowed to re-pressurize until any bubbles are reabsorbed. Media is then used to submerge the device, e.g., IMDM+20% FBS.

After the device is primed, the fluid sample of interest is introduced into the sample loading chamber 150 of the device. For example, using gel-loading tips, samples of whole blood (or samples containing isolated motile cells) can be pipetted into the sample loading chamber 150. Once the fluid sample is in place in the chamber 150, some of the desired cells migrate into the passageways 115 of the baffle filter 125 and then into the migration channels 120 of the device. Static fluid pressure can also cause some of the cells of the sample to move, e.g., by granular flow (e.g., like grains of sand tumbling down an incline) into the passageways 115 of the baffle filter 125, where the desired motile cells begin migrating into the device.

Various properties of the motile cells can be monitored in the device including, for example, any of the spontaneous migration patterns provided in Table 2. In some implementation, one or more of the following migration patterns are monitored in the device: the number of spontaneously migrating neutrophils; the number of neutrophils that undergo a migratory oscillation; the number of neutrophils that undergo a migratory pause; whether neutrophils reverse their migration; the average distance migrated by neutrophils; the maximum migration distance; the mean velocity of neutrophils; the mean acceleration of neutrophils; the mean distance of oscillatory migration; the mean forward migration of neutrophils away from the migration chamber, e.g., maze, entrance; the mean vertical migration of neutrophils parallel to the migration channels; the mean horizontal migration of neutrophils perpendicular to the migration channels; and the mean nucleus size of migrating neutrophils.

During the migration assays, the device 100 can be maintained at a temperature suitable for cell migration. For example, in the case of neutrophil migration, the device 100 can be placed in a biochamber and heated to about 37° C. and having a 5% CO2 atmosphere with 80% humidity to maintain the viability of the cells. The humidified environmental chamber can, in certain implementations, increase the observation duration by several hours.

Automated Cell Tracking and Analysis

The devices disclosed herein are designed to be imaged using an automated fluorescent inverted compound microscope, but imaging can be performed using any commercially available brightfield/Differential Interference Contrast (DIC) setup in combination with a brightfield tracking algorithm. Each device can incorporate multiple imaging fields, e.g., at least 2, 4, 5, 6, 7, or 8, or more imaging fields. If monitoring a large number of fields, XY points can be set prior to loading the samples into the device. An additional field in the central sample loading chamber can be imaged to facilitate normalization of neutrophil numbers present in a loaded sample, so that comparisons of cell motility data collected from different samples loaded in different devices can be made.

An imaging device is used to capture neutrophil migratory behaviors over a span of time from a single microfluidic device. For example, the imaging device can be any microscopy system, but preferably an inverted microscope with bright field or phase illumination. The imaging device can include a 37° C. heated stage or incubation chamber, a time-lapse camera, and an automated stage to move the device to pre-defined locations to increase the number of cells observed in one device. However, non-optical methods can also be used to monitor the migration of neutrophils in a microfluidic device, e.g., the use of electrodes integrated into migration channels to measure electrical impedance, or by measuring displacement of magnetic particles in the channels to measure alterations the magnetic field. Each viewing field is captured repeatedly at any time interval that allows accurate tracking of neutrophil migration, e.g., every 30 seconds, 1 minute, 2 minutes, 3 minutes, 4 minutes, 5 minutes, 10 minutes, or more. The total time required to record the movement of the motile cells in the device depends on various factors, including the speed at which cells spontaneously move into the device, the baffle passageway length, and the migration channel length. In one example, the assays are run for 4 or more hours to allow time for the blood droplet to spread throughout the central sample loading chamber and cells to migrate through the maze. Longer or shorter monitoring times also can be required, depending on the nature of the particular assay being conducted. For example, the time to monitor motile cell movement in the device (e.g., neutrophil movement) can be on the order of 10 minutes, 20 minutes, 30 minutes, 40 minutes, 50 minutes, 1 hour, 2 hours, 3 hours, 5 hours, 6 hours, 7 hours, 8 hours, 9 hours, 10 hours, or longer.

The system can further include a computer system that is operatively coupled to the imaging system. The computer system can include a tangible computer-readable storage medium (for example, a hard disk and the like) that stores computer program instructions executable by data processing apparatus (for example, a computer system, a processor, and the like) to perform operations. The operations can include controlling the imaging system to capture images of the migration of cells through the device over time, e.g., through the migration channels and migration chamber. In addition, the computer system can receive the captured images from the imaging system, and process the images to obtain various parameters, e.g., one or more of a migration speed of motile cells, the directionality of motile cells, and consistency in the speed and directionality of the cells, e.g., changes in direction such as oscillations and reverse migrations and/or changes in speed such as pausing. The different behaviors of motile cells, e.g., particular neutrophil spontaneous migration parameters, can be quantified by counting the number of motile cells that exhibit the particular behaviors.

In general, computer systems suitable for the execution of a computer program include, by way of example, general or special purpose microprocessors or both, or any other kind of central processing unit. Generally, a central processing unit will receive instructions and information from a read-only memory or a random access memory or both. The essential elements of a computer system are a central processing unit for performing or executing instructions and one or more memory devices for storing instructions and information. Generally, a computer system will also include, or be operatively coupled to receive information from or transfer information to, or both, one or more mass storage devices for storing information, e.g., magnetic, magneto optical disks, or optical disks.

Computer-readable media suitable for storing computer program instructions and information include various forms of non-volatile, tangible memory, media, and memory devices, including by way of example semiconductor memory devices, e.g., EPROM, EEPROM, and flash memory devices; magnetic disks, e.g., internal hard disks or removable disks; magneto optical disks; and CD ROM and (Blue Ray) DVD-ROM disks. The processor and the memory can be supplemented by, or incorporated in, special purpose logic circuitry.

To provide for interaction with a user, implementations of the subject matter described in this specification can be implemented on a computer system having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well. In addition, a computer system can interact with a user by sending documents to and receiving documents from a device that is used by the user; for example, by sending web pages to a web browser on a user's client device in response to requests received from the web browser.

Implementations of the subject matter described in this specification can be implemented in a computer system that includes a back end component, e.g., as an information server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the computer system can be interconnected by any form or medium of digital information communication, e.g., a communication network. Examples of communication networks include a local area network ("LAN") and a wide area network ("WAN"), e.g., the Internet.

The computer systems can use various software packages to track the movement of the cells and to analyze and characterize those movements. In one specific example, cells were tracked using ImageCV®, TrackPy®, and SciKit-Learn® packages in Python software, but other object tracking software can be used. The code requires an Audio Video Interleaved (AVI) input. The initial processing allows for cell tracking in brightfield images. The background is removed and cells are tracked by size, velocity, and directionality. These tracks can be written to individual comma separated value (CSV) files for each imaging field. The specific variables for each track can include: track number, video frame, cell diameter, x position, y position, distance, and velocity.

Post-capture analysis of the images obtained from a single microfluidic device can be used to measure and quantify any number of the migratory parameters present in Table 2, for the purposes of assigning a score to each parameter so as to diagnose sepsis.

In some implementations, the computer system is configured to execute computer software applications that perform machine learning and statistical analyses of the data captured by the imaging system. For example, the computer system can be configured to perform multivariate analysis to determine correlations between neutrophil migration speed and clinical parameters.

In some implementations, the microfluidic device is incorporated into a disposable casing or cartridge that may be inserted into a system that includes an imager that is coupled to a computer system for analysis, e.g., time-lapse imaging and analysis of cell motility patterns. For example, the microfluidic device in a cartridge can be inserted in a standalone imaging device coupled to or including a computer system. A blood sample is added to the device for time-lapse imaging and analysis to determine the Sepsis Score. When the analysis is complete, the cartridge containing the used microfluidic device is removed from the imaging device and can, in some embodiments, be disposed.

Figure 5:
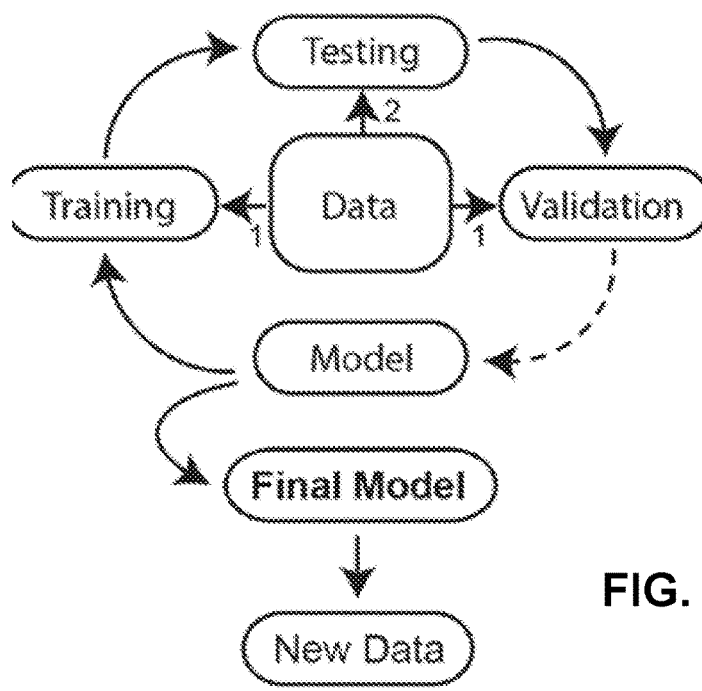
FIG. 5 is a flow chart of an example of a machine learning approach to develop a Sepsis Score for diagnosing sepsis.
Figure 6A:
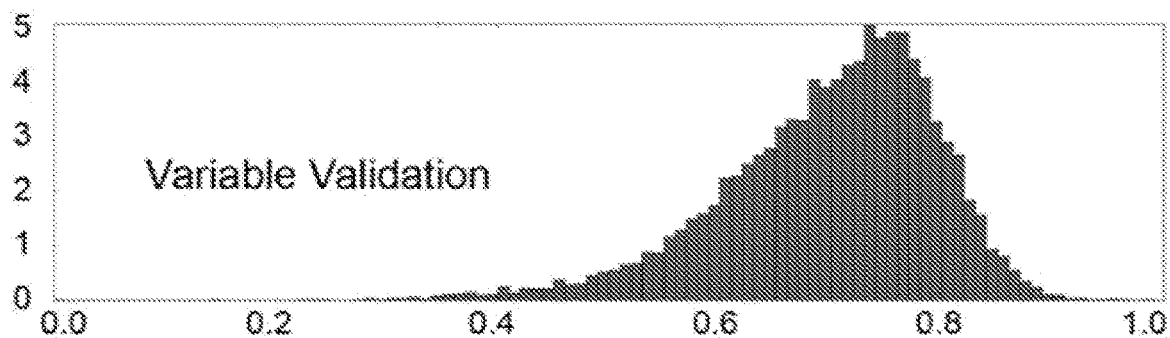
FIGS. 6A and 6B are a pair of graphs that show that the model variables were validated independently, and in combination.
Figure 6B:
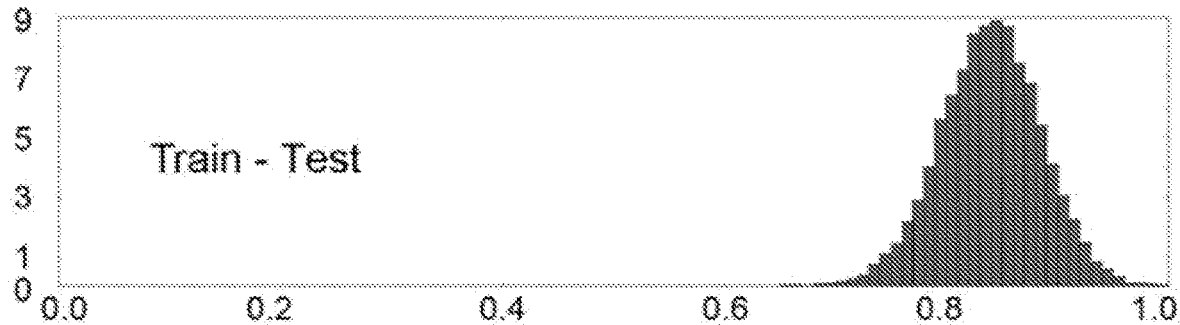

FIG. 5 provides a flow chart of an approach to develop and optimize a machine learning model that can identify which spontaneous neutrophil migration parameters can be used in combination to diagnose sepsis with a high degree of accuracy. Data collected from observation of each spontaneous neutrophil migration parameter provided in Table 2 can be split 1:2:1 for training, testing, and validation steps in model development. The algorithm is trained on the training data. Then, variables were changed and significant variables were determined with testing data. These variables include number of cells, migration distance, oscillations, reverse migration, and pausing. With these variables, final graphs and results are produced with the held-out set. T-distributed stochastic neighbor embedding (tSNE) graphs are produced to visually confirm split of data by groups (sepsis, pre-sepsis, non-sepsis, and SIRS). Finally, the test-train split is changed and the analysis is run 500-1000 times and a histogram of the area under the radio operating characteristic (AUROC) values from the held-out data is graphed. FIGS. 6A-B show that each variable was validated independently (variable validation), and then in combination (Train-Test) to optimize the model.

The machine learning analysis disclosed herein results in an optimized model, or "Sepsis Score," based on the scoring of one or more particular neutrophil spontaneous motility parameters that are predictive of sepsis in a subject. For example, a scoring system that integrates five specific neutrophil behaviors (the number of spontaneously migrating neutrophils; the number of migratory oscillation events (N); the number of migratory pausing events (P); the number of oscillation events (O); the number of reverse migration events (R); and the average distance by which the neutrophils travel (AD)) into the following equation:

$$\text{Sepsis Score} = \frac{N(O + P + R + AD)}{10^3},$$

can be used to diagnose sepsis. However, the scoring system can integrate any one or more of the neutrophil motility parameters present in Table 2 to diagnose sepsis. In some implementations, one of any one of N, O, P, R, AD, MD, V, A, OD, F, VM, HM, or S is scored for a blood sample so as to predict sepsis. In some implementations, any two or more of N, O, P, R, AD, MD, V, A, OD, F, VM, HM, or S are scored for a blood sample so as to predict sepsis.

For example, the scoring system can integrate one or more of the number of spontaneously migrating neutrophils, the number of migratory oscillation events, the number of migratory pausing events, the number of reverse migration events, the average distance by which the neutrophils travel, the maximum migration distance, the mean velocity of neutrophils, the mean acceleration of neutrophils, the mean distance of oscillatory migration, the mean forward migration of neutrophils away from the migration chamber, e.g., maze, entrance, the mean vertical migration of neutrophils parallel to the migration channels, and the mean nucleus size of migrating neutrophils. One of skill in the art would understand that the particular selection of both the total number of motility parameters and specific motility parameters for integration in the scoring model will affect the accuracy of the model in diagnosing sepsis. In some implementations, one motility parameter from Table 2 is included in the Sepsis Score. In some implementations, 2, 3, 4, 5, 6, 7, 8, 9, 10, 11, 12, or 13 motility parameters from Table 2 are included in the Sepsis Score.

In some implementations, a sepsis score of 30 or above indicates that a subject has sepsis or will develop sepsis. However, the Sepsis Score can be any score that can be used to diagnose sepsis in a subject based on the monitoring of neutrophils from a blood sample from the subject using the methods and devices disclosed herein. For example, in some implementations, the Sepsis Score can be 5, 10, 15, 20, 25, 30, 35, 40, 45, 50, 55, 60, 65, 70, 75, 80, 85, 90, 95, 100, or higher. In some implementations, the Sepsis Score can be between 5 and 20, between 15 and 30, between 25 and 40, between 35 and 50, between 45 and 60, between 55 and 70, between 65 and 80, between 75 and 90, or between 85 and 100.

Applications

The microfluidic devices and methods described herein can be used in various applications. The devices provide a platform for measuring the directionality and velocity of motile cells for the purposes of detecting and quantifying abnormal motility phenotypes, and determining the extent of damage to motile cells. For example, the devices and methods can be used to assay samples from patients with injuries that put them at high risk of having impaired neutrophil function, e.g., over-stimulated neutrophils with impaired neutrophil directionality, so as to determine whether the patient is at enhanced risk of neutrophils migrating to healthy tissues to cause further injuries.

In some implementations, the devices and methods disclosed herein can be used to diagnose a particular disease or ailment, such as sepsis or Systemic Inflammatory Response Syndrome (SIRS) or SIRS-like disorders, or predict the whether a patient is more likely to develop the particular disease or ailment. For example, the devices and methods provide a platform to analyze neutrophil motility in subjects that are suspected of having sepsis or developing sepsis, e.g., hospital patients who have are at risk of developing an infection, such as ICU patients, patients with burn injuries or tissue trauma, patients undergoing chemotherapy, or patients with diabetes. The device can be used to test the whole blood of patients suspected of having sepsis, or determine to be at an increased risk of developing sepsis. An increase in one or more of the spontaneous migration parameters provided in Table 2 that establish a Sepsis Score above a certain threshold (e.g., 30 or more) indicates that the subject has sepsis or will develop sepsis.

In some implementations, sepsis can be detected in a patient sample 1 to 5 days before the patient develops clinical signs of sepsis. In some implementations, the sepsis can be detected 1 day before a patient develops clinical signs of sepsis. In some implementations, the sepsis can be detected 2 days before a patient develops clinical signs of sepsis. In some implementations, the sepsis can be detected 3 days before a patient develops clinical signs of sepsis. In some implementations, the sepsis can be detected 4 days before a patient develops clinical signs of sepsis. In some implementations, the sepsis can be detected 5 days before a patient develops clinical signs of sepsis.

The methods and devices disclosed herein can be used in a clinical context to determine whether a human or animal subject has sepsis or is more likely to develop sepsis. For example, the methods and devices described herein can be used in a point-of-care clinical setting such as at a hospital or veterinary hospital. The devices can be used on samples of whole blood without requiring a separate isolation step for the neutrophils, thus reducing processing time. In addition, the use of whole blood preserves the natural environment for neutrophils without inducing neutrophil activation, thereby preserving the motility phenotype of neutrophils in sepsis samples. The devices can be designed to handle small quantities of fluid sample, e.g., samples having a volume of about 1 microliter. The devices can be used with blood obtained from humans or animal subjects. Both the reductions in sample processing time due to the use of whole blood, and the reduced sample volume requirements for the assay, are advantageous for clinical applications, where it may not be feasible to obtain larger amounts of sample fluid, e.g., in infants or small mammals.

In some implementations, the methods and devices disclosed herein can be used in a veterinary setting to determine whether an animal, e.g., a mammal, has sepsis or is at a risk of developing sepsis. For example, the devices can be used to determine whether a domestic animal that has been injured, has an infection, or has suffered from some other trauma, has sepsis or is more likely to develop sepsis. In some implementations, the animal can be a dog, a cat, a bird, a horse, a pig, a sheep, a goat, a cow, a buffalo, or an alpaca.

In some implementations, the devices can be used to analyze efficacy of one or more medications used to treat sepsis. For example, the devices can be used to monitor a patient receiving a treatment for sepsis to determine whether the treatment is effective in reducing infection. The medication can include, but is not limited to, one or more antibiotics, corticosteroids, and vassopressors. One or more antibiotics and fluids are typically administered as soon as a patient is identified as having sepsis. In most cases, a broad-spectrum antibiotic is administered first since the specific bacterium causing the infection has not been identified. A more focused antibiotic is administered once the specific bacterium is identified. Corticosteroids can also be administered to some patients to reduce inflammation and depress the immune system, although they are not effective for all patients. Vassopressors can also be administered to increase blood pressure.

Blood samples can be obtained from the patient once or periodically after administration of the drug. Using the devices and methods described herein, neutrophil activity can be analyzed to determine the drug's effect on neutrophil motility. In particular, one or more spontaneous neutrophil motility parameters provided in Table 2 can be quantified to determine whether the neutrophils have begun to exhibit a motility phenotype more similar to that of healthy, normal cells. In some situations, neutrophils obtained from a subject can be studied over a one-week period, for example, obtained at 24 hour intervals. If the neutrophils do not begin to exhibit the normal migratory behaviors of healthy cells, then the sepsis treatment can be altered such that a different quantity of the medication is administered or a different drug is administered. The efficacy of the altered treatment can then be tested using the device. To determine a long-term effect of sepsis and treatment on the subject, the study period can be expanded to longer periods, e.g., six months, at regular intervals.

In some implementations, the devices and methods disclosed herein can be used to screen for novel treatments for sepsis. For example, devices loaded with a whole blood sample from a sepsis patient can be used to test the effect of hundreds, 1000s, 10,000s, or 100,000s of small molecules or other chemical agents on the cell motility of neutrophils, e.g., spontaneous cell motility of neutrophils. Macromolecules such as proteins, e.g., antibodies, can also be tested in this system. Reversion of the spontaneous motility of neutrophils seen in sepsis to a phenotype closer to that of neutrophils in healthy patients would indicate that tested molecule could potentially be a sepsis treatment. For example, the devices and methods can be used to screen compounds to see which, if any, have an effect on any one or more of the cell motility parameters provided in Table 2.

EXAMPLES

The invention is further described in the following example, which do not limit the scope of the invention described in the claims.

Example 1

Device for Monitoring Neutrophil Motility in Whole Blood

To understand whether physical trauma, infection and/or sepsis affects neutrophil motility patterns, microfluidic devices with channels and mazes were designed to monitor the migratory behaviors of neutrophils directly from whole blood samples, without the use of chemical attractants for neutrophils.

Device Fabrication

Devices were designed using AutoCAD. Chrome masks for photolithography were printed by FrontRange Imaging (Boulder, Colo.). Silicon wafers were spin-coated with two layers of negative photoresist (SU-8, Microchem, Newton, Mass.), the first layer was 5 μm thick and the second layer was 50 μm thick. The wafers were then patterned by sequential UV exposure through two photolithography masks, and processed per manufacturer's instructions. The patterned wafers were then used as a mold for PDMS (Polydimethylsiloxane, Fisher Scientific, Fair Lawn, N.J.) to produce the final PDMS devices. Central inlets were punched using a 1.2 mm punch (Harris Uni-core™) and the whole device cut out using a 5 mm punch. Devices were then irreversibly bonded to glass-bottom well plates (Mattek, Ashland, Mass.).

FIG. 2A shows a macroscopic image of the microfluidic device with scale, and FIG. 2B provides a schematic of the device, including a close-up illustration of the central sample loading chamber and the 8 migration blocks. Each migration block is composed of a baffle filter with about 18 baffle passageways that are at least 50 μm in length and 4.5 μm wide. The baffle passageways are connected to a series of about 19 migration channels that are approximately 500 μm in length that run directly into a migration chamber that is approximately 150 μm wide and 640 μm long. The migration chamber is subdivided by a series of barriers to create a grid-like series of passages that enable the neutrophils to migrate in up to 4 different possible directions, thereby providing the neutrophils with opportunities to change direction, e.g., reverse migration. The migration channels and the migration chamber were designed to be 10 µm wide and 10 µm high. Neutrophil motility is monitored in the migration channels and in the migration chamber.

The device was then tested to see if it could be used for monitoring the motility of neutrophils from whole blood effectively.

Pre-Assay Preparation

Prior to the addition of a blood sample, devices were primed with IMDM containing 10% FBS and 1% Fibronectin (from human plasma, Sigma) by pipetting 50 µl into the sample loading chamber and around each device, such that a dome of liquid formed on top, and the outer edge of the device in contact with the coverslip was surrounded. The devices were placed under a vacuum for at least 10 minutes, and then removed and allowed to re-pressurize and equilibrate for at least 15 minutes to remove bubbles.

Whole Blood Handling

Peripheral blood samples from patients were drawn in 10 mL Heparin-coated vacuum tubes (Vacutainer, Becton Dickinson) from indwelling lines. Peripheral blood from healthy volunteers aged 18 years or older was also collected in Heparin-coated vacuum tubes (Research Blood Components). Some blood samples were split for comparison between the two assays using whole blood (1 mL) and isolated neutrophils (9 mL). Blood was tested in the device within the first 3 hours after being collected because neutrophil activity declines as the blood ages.

Whole blood samples to be loaded in the device were diluted 1:1 in IMDM with 20% FBS and stained with Hoechst 33342 dye at 32 µM for 15 minutes prior to loading. A small droplet of 0.5 µL of stained blood was then pipetted into the center of the device using a gel-loading tip. The blood droplet is pipetted into the central chamber and time-lapse imaging of the mazes was then used to measure neutrophil behavior over a period of 4 hours.

Device Operation

FIGS. 3A-D show still images from a time-lapse movie illustrating that when a small volume of blood (~1 µL) is applied to the sample loading chamber, the baffle filter of the device selectively allowed neutrophils to pass through the filter and enter the migration channels, while preventing RBCs from entering the assay field. The baffle filter blocked RBCs from migrating into the migration channels with the neutrophils. Thus, FIGS. 3A-D show that the device as designed with a baffle filter allows neutrophils from whole blood to enter the device for observation, while effectively excluding RBCs from entering the device.

Example 2

Spontaneous Motility of Neutrophils in Sepsis

To understand whether analysis of neutrophil motility in whole blood could be used to diagnose or predict sepsis, the microfluidic device of Example 1 was used to analyze whole blood samples collected from healthy donors and from hospital patients having injuries or infections that make them susceptible to sepsis. The patterns of neutrophil motility were observed using time-lapse imaging for each subject population, quantified, and then compared using machine learning techniques to determine whether particular neutrophil motility parameters can be predictive of sepsis.

Imaging Cell Motility

Cell motility was imaged at 10× magnification using a fully automated fluorescent Nikon TiE inverted wide field microscope with a biochamber heated to 37° C. with 5% $CO_2$. Each microfluidic device included 8 imaging fields, each containing one migration migration chamber. Each field was imaged every 2 minutes over the course of 4 hours to allow accurate tracking of cell motility.

FIGS. 4A-D provide still images extracted from a time-lapse movie of spontaneous migration of neutrophils from a blood sample from a septic patient. Once the neutrophils passed through the baffle filter, neutrophil velocity, directional choices, and persistence of velocity and direction were measured in the migration channels and in the migration chamber with high precision. The track lines in the panels of FIGS. 4A-D show examples of particular spontaneous motility behaviors that were observed, including reverse migration, oscillation, and pausing. Thus, FIGS. 4A-D illustrate that particular neutrophil motility behaviors can be identified and measured from whole blood using the microfluidic device.

Machine Learning and Statistical Analysis

Automated cell tracking was performed using ImageCV, TrackPy, and SciKit-Learn packages in Python. Files were converted to standard AVI format using Nikon Elements or ImageJ. Initial processing was performed to allow brightfield tracking and included removing the background. Cell tracking was performed automatically from brightfield images for most of the time-lapse sequences. Cells were tracked by size, velocity, and directionality. These tracks were written to individual CSV files for each imaging field. The specific variables for each track included: track number, video frame, cell diameter, x position, y position, distance, and velocity. Cell motility pattern identification and definitions are detailed in Table 2. Figures were prepared using Illustrator CS5 Version 15.0.0 (Adobe Systems).

Unsupervised learning was performed to understand inherent biases in the dataset, and then supervised learning was used to identify and validate new spontaneous migration parameters to identify sepsis. First, self-organizing feature maps (SOFMs) were applied to determine natural clustering in the data and to understand the bias due to individual runs, e.g., lighting, positioning of the chip in the microscope, and individual patient draws. The similarity was measured using distance metrics through Mahalanobis distance, and Euclidean distance was visualized with t-distributed stochastic neighbor embedding (t-SNE). Once these biases were determined, SOFMs were run with the neutrophil motility parameters that had previously been determined to predict sepsis using isolated neutrophils (see, e.g., Jones et al., Spontaneous neutrophil migration patterns during sepsis after major burns, *PloS One* 9(12):e114509 (2014)).

Support vector machines (SVM) were then used to differentiate septic from non-septic patients in a derivation cohort. To further optimize the sepsis classification parameters, regularized linear discriminant analysis was applied via hold-out analysis with cross validation and multiple resampling due to the few samples and increasing number of parameters. With these parameters, error estimation was applied to all possible subsets to find the parameters that resulted in the highest accuracy sepsis prediction. To further validate the integrative score, the equation was applied to an independent validation cohort of critically ill patients with and without sepsis.

FIG. 5 depicts a flow chart of a machine learning process used to identify migration patterns specific to sepsis. Analysis applied machine learning algorithms to produce t-SNE graphs and a histogram area under the receiver operator characteristic (AUROC) curves for machines were trained on the testing data. Briefly, the data was split 1:2:1 (training data: testing data: held-out set) by patient. The algorithm was trained on the training data. Then, variables were changed and significant variables were determined with testing data. These variables include number of cells, spontaneous motility distance, oscillations, reverse migration, and pausing. With these variables, final graphs and results were produced with the held-out set. tSNE graphs were produced to visually confirm split of data by groups (sepsis, pre-sepsis, non-sepsis, and SIRS). Finally, the test-train split was changed and the analysis is run 500-1000 times and a histogram of the AUROC values from the held-out data is graphed. FIGS. 6A-B illustrate that each variable was validated independently (variable validation), and then in combination (Train-Test) to optimize the model.

tSNE analysis is applied for dimensionality reduction and visualization of high-dimensional datasets. The technique allows visualization of the effect various variables have on separation of the different data subsets. AUROC values are calculated from ROC curves created from each train-test split. These values are then plotted on a histogram from 0 to 1. The average AUROC is reported as the accuracy of the given model.

The number of subjects needed to test the hypothesis that the level of performance for the proposed Sepsis Score can significantly improve current diagnostic standards was calculated using asymptotic variance equations (Margaret Sullivan Pepe, The Statistical Evaluation of Medical Tests for Classification and Prediction, Oxford University Press, 16 Dec. 2004). For the calculations, $\alpha=0.05$ was chosen as the desired minimum type 1 error rate, $\beta=0.1$ the desired minimum type 2 error rate (90% study power). The sensitivity (64%) and specificity (65%) for sepsis of 2016 Sepsis-3 diagnostic criteria were employed as reference. The desirable sensitivity and specificity levels for the proposed Sepsis Score were estimated from the first part of the study as 99% and 97%, respectively.

For comparison of patient samples, values are presented as a Tukey boxplot, with the bottom and top of the box representing the first and third quartiles respectively, and the central line the second quartile (median). Bottom and top whiskers represent the lowest and highest datum within 1.5 interquartile range respectively. For statistical analysis, groups were compared using a One-way ANOVA with Tukey's multiple comparison test. Graphing and statistical tests were performed using Prism 7.0a software (GraphPad Software Inc.).

Results

A machine learning approach was used to identify the predictive values for individual neutrophil migration parameters. Table 3 shows the AUROC values, the percent sensitivity, and % specificity for five individual neutrophil migration parameters. The results in Table 3 show that individual neutrophil migration parameters can predict sepsis in the derivation cohort accurately. For example, the oscillations parameter scored alone has a specificity level of 100% and a sensitivity level of 95%.

TABLE 3

| Parameter | AUROC | % Sensitivity | % Specificity |
|---|---|---|---|
| Number of spontaneously migrating neutrophils | 0.93 | 100 | 68 |
| Oscillations | 0.97 | 100 | 95 |
| Pausing | 0.96 | 100 | 81 |
| Reverse Migration | 0.94 | 100 | 68 |
| Average Distance | 0.75 | 100 | 24 |

We reasoned that a scoring system that incorporates multiple neutrophil migration parameters will be more accurate than any one parameter alone. An optimized sepsis scoring system that incorporated five neutrophil migration parameters was developed that enabled the diagnosis of sepsis in a whole blood samples with significant accuracy. Specifically, the Sepsis Score highly predictive of sepsis integrates the following neutrophil migration parameters: the number of spontaneously migrating neutrophils (N), oscillations (O), pausing (P), reverse migration (R), and average distance (AD) into the following calculation:

$$\text{Sepsis Score} = \frac{N(O + P + R + AD)}{10^3}.$$

A Sepsis Score of 30 or above indicates that the subject from whom the assayed blood sample was collected has sepsis.

Figure 7:
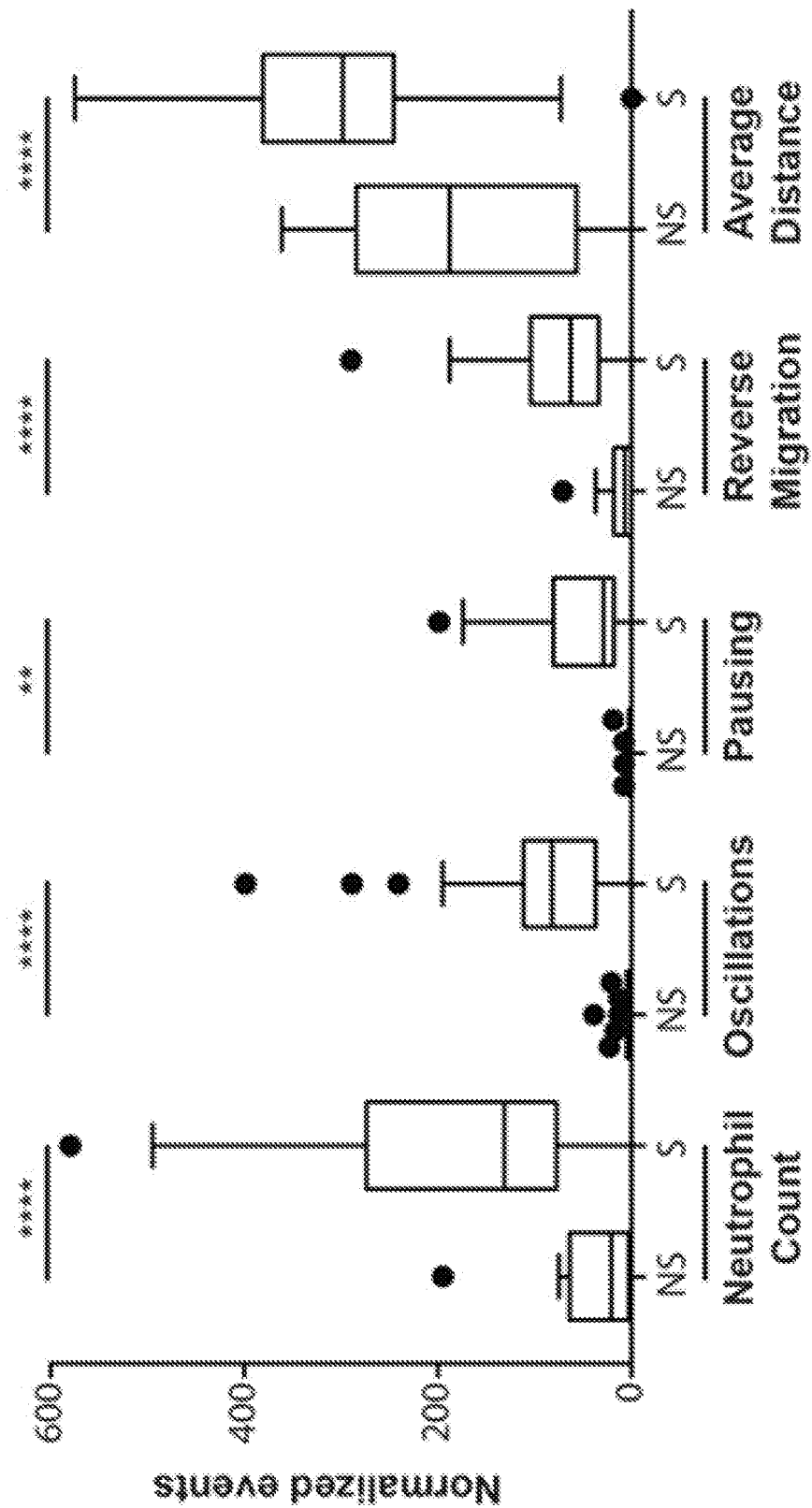
FIG. 7 is a box plot of neutrophil behaviors per device for non-septic and septic patient samples, normalized by neutrophil count.

FIG. 7 shows that Septic Scores were significantly higher for five neutrophil migration parameters quantified for neutrophils from septic patient blood samples when compared to scores for neutrophils from non-septic patient blood samples (N–87 samples; N–23 patients). More specifically, the septic scores for the number of spontaneously migrating neutrophils, the number of oscillation events, the number of pausing events, reverse migration, and the average distance traveled were higher significantly for the sepsis samples. Neutrophil behaviors per device for non-septic and septic patient samples were normalized by the neutrophil count in the central chamber. Box and whisker plots: Tukey's boxplot. Statistics: One-way ANOVA with Tukey's multiple comparisons test. $p \leq 0.01$, **$p \leq 0.001$. The results of FIG. 7 demonstrate that a number of particular neutrophil migration parameters are identifiable specifically in sepsis blood samples relative to non-sepsis blood samples, and can be successfully quantified to diagnose sepsis.

Example 3

Comparison of Whole Blood Assays to Isolated Neutrophils

The biology underpinning activation of neutrophils during sepsis is poorly understood. To test whether neutrophil migration assays using whole blood are more accurate in predicting sepsis than assays using isolated neutrophils, the results from whole blood and isolated neutrophil assays that were run in parallel were compared. Samples from septic and non-septic patients were run for both the whole blood and isolated neutrophil assays.

Whole blood samples were prepared and handles according to the procedures described in Example 2. For isolated neutrophil assays, the neutrophils were isolated from 9 mL of whole blood by density separation and negative selection (Neutrophil Enrichment Kit, STEMCELL Technologies, Vancouver, Canada). Cells were then stained with 32 μM Hoechst 33342 dye for 10 minutes, washed, and re-suspended in IMDM+20% FBS at $2.0 \times 10^7$ cells/mL prior to loading into the device. Isolated neutrophils were loaded in the device by pipette using a gel-loading tip until cells were observed to exit the device outlet.

FIGS. 8A-E are a series of plots comparing the results from whole blood and isolated neutrophils assays run in parallel for non-septic and septic patient samples, wherein five neutrophil migration patterns were monitored. All five of the neutrophil migration parameters tested were scored significantly higher when the whole blood samples were assayed than when the isolated neutrophils were assayed.

More specifically, the neutrophil migration parameters assayed were the number of spontaneously migrating neutrophils (N), oscillations (O), pausing (P), reverse migration (R), and average distance (AD). For example, neutrophils from sepsis whole blood samples exhibited many more oscillation events than the neutrophils from non-septic whole blood samples. By contrast, isolated neutrophils from sepsis patient samples showed a very small increase in the number of oscillations compared to isolated neutrophils from non-sepsis patient samples. In addition, reverse migration and average distance are significantly correlated with sepsis when whole blood samples were tested, but negatively correlated with sepsis when isolated neutrophils were tested. (N=87 samples, N=23 patients). Error bars: Mean±SEM. The results of FIGS. 8A-E therefore indicate that assays using whole blood samples more accurately diagnose sepsis than assays that use isolated neutrophils.

Tests were also conducted to determine whether plasma factors in the blood of septic patients are responsible for the observed neutrophil spontaneous motility, and is responsible for the greater accuracy of whole blood assays in diagnosing sepsis. The marked increase in accuracy for the whole blood assay compared to isolated cells, raised the possibility that the difference was due to non-cell-autonomous pathways. To test this possibility, a series of experiments were performed in which plasma components were exchanged between healthy and septic blood samples.

For plasma-swapping experiments, 1 mL of whole blood was centrifuged at 200 g for 10 minutes to pellet cells. The platelet-rich plasma supernatants were then drawn from the tubes and transferred into fresh tubes. Platelets were then pelleted at 1900 g for 10 minutes and the plasma fraction drawn into fresh tubes. Cell pellets were then re-suspended in the appropriate exchanged plasma and an aliquot loaded into the device. For blood-spiking experiments, immune-modulators were added to the media at 2× the target dose prior to mixing 1:1 with whole blood. Once mixed, spiked blood samples were incubated at 37° C. for 30 min prior to loading.

Figure 9B:
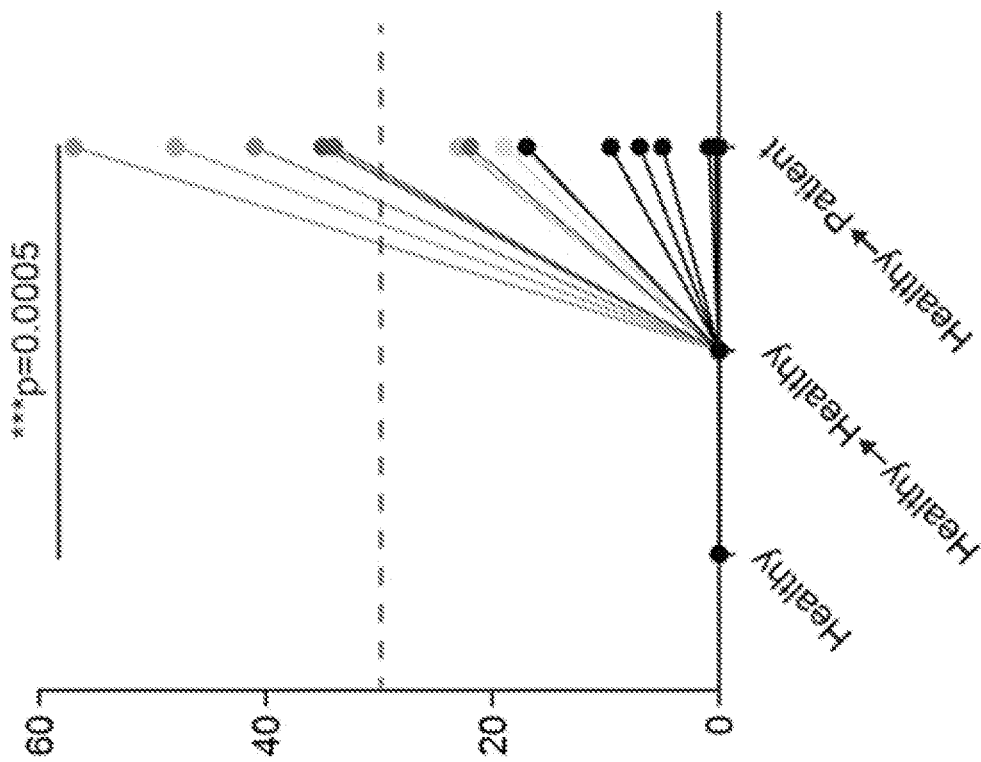
FIGS. 9A and 9B are a series of graphs that show the results of plasma transfer experiments to determine if plasma factors drive spontaneous neutrophil migration.
Figure 9A:
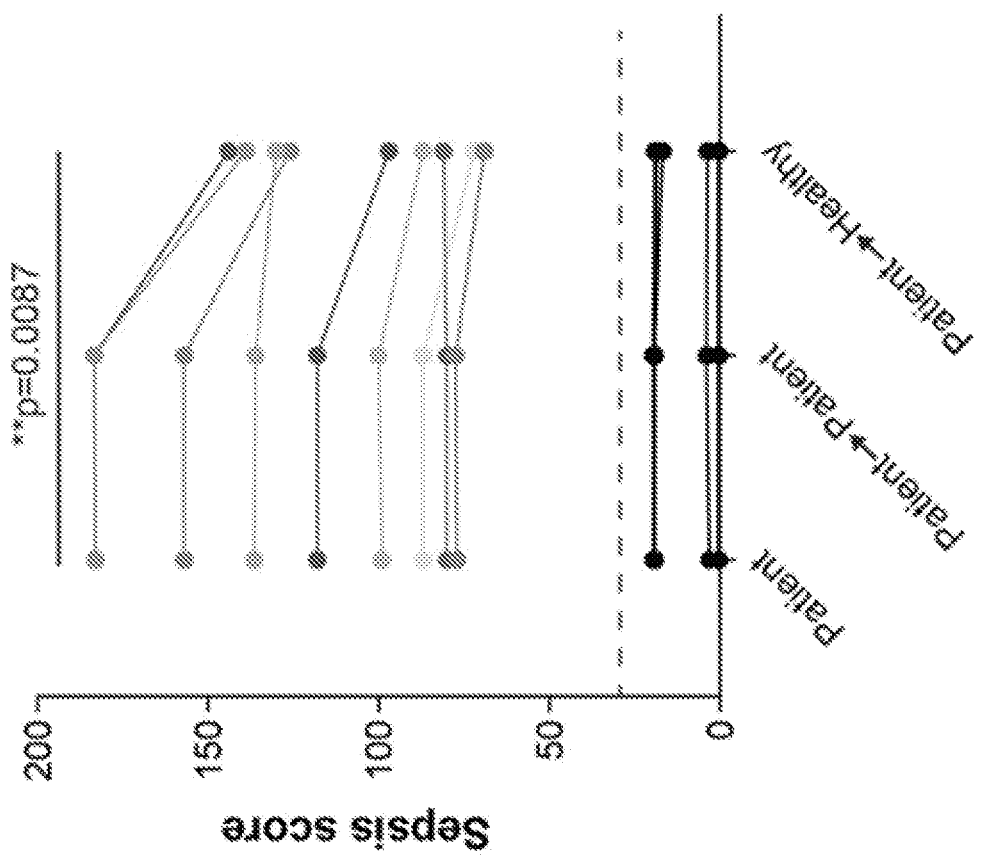

FIGS. 9A-B show that plasma factors drive spontaneous neutrophil migration. Neutrophils from septic blood continued to exhibit spontaneous motility in the presence of healthy plasma (FIG. 9A), confirming that cell-autonomous pathways in septic neutrophils are not inhibited by factors present in healthy plasma. The transfer of patient blood cells into plasma from healthy donors reduced sepsis scores, but the scores for septic patients remain within the septic range. The transfer of healthy blood cells into patient plasma (FIG. 9B) significantly increased sepsis scores, with ⅝ transferred into plasma from septic patients achieving scores within the septic range (>30, dashed red line). N=15 (8 septic). Statistics: Paired t-test. Neutrophils from healthy blood displayed spontaneous motility patterns after incubation in septic plasma, demonstrating that non-cell-autonomous signals are also present in septic blood. Spontaneous motility was not stimulated by the presence of non-autologous plasma or the experimental procedure, as exchanging plasma between healthy blood samples did not result in stimulation of spontaneous neutrophil motility. The results of FIG. 3B show that plasma factors present in the blood of septic patients contribute to the specific alterations of neutrophil functionality in sepsis that are captured using the whole blood assay.

Moreover, Table 4 illustrates attempts to recapitulate a sepsis-like neutrophil phenotype by spiking whole blood with various individual immune-modulators, which were previously reported to be elevated in septic blood, were unsuccessful at inducing spontaneous motility patterns. These observations suggest that neutrophils integrate multiple signals over time when exposed to the altered blood environment present during sepsis, which ultimately induces the spontaneous motility patterns we observed.

TABLE 4

| Treatment | Conc. [ng/mL] | Number of samples | Spontaneously migrating cells (N) | Oscillations (O) | Pausing | Treatment | Conc. [ng/mL] | Number of samples |
|---|---|---|---|---|---|---|---|---|
| IFN-γ | 1.8 | 10 | 10.8 ± 12.4 | 4.8 ± 6.3 | 7.0 ± 6.9 | 4.1 ± 4.2 | 302 ± 83 | 3.4 |
|  | 2.5 | 3 | 0 ± 0.0 | — | — | — | — | 0 |
| TNF-α | 0.1 | 10 | 7.2 ± 13.9 | 1.7 ± 3.4 | 4.8 ± 8.8 | 4.1 ± 6.4 | 331 ± 331 | 2.5 |
|  | 0.5 | 3 | 25.3 ± 26.1 | 1.3 ± 1.2 | 15.7 ± 14.2 | 14.7 ± 10.8 | 275 ± 86 | 7.8 |
|  | 1.0 | 3 | 2.7 ± 1.2 | 0.7 ± 1.2 | 1.3 ± 0.6 | 1.0 ± 1.7 | 174 ± 92 | 0.5 |
| G-SCF | 0.3 | 10 | 6.7 ± 13.6 | 4.2 ± 9.7 | 4.7 ± 9.6 | 2.4 ± 4.8 | 337 ± 337 | 2.4 |
|  | 0.5 | 3 | 2.3 ± 2.3 | 0.3 ± 0.6 | 2.0 ± 1.7 | 0.7 ± 1.2 | 231 ± 143 | 0.6 |
| IL1-β | 0.1 | 10 | 3.8 ± 3.2 | 1.4 ± 1.5 | 2.4 ± 2.8 | 1.8 ± 1.8 | 272 ± 177 | 1.1 |
|  | 1.0 | 3 | 0.3 ± 0.1 | 1.0 | 1.0 | — | 253 ± 10 | 0.1 |
| LPS | 0.2 | 10 | 4.8 ± 5.6 | 2.0 ± 2.7 | 4.4 ± 5.2 | 1.6 ± 1.7 | 155 ± 88 | 0.8 |

Example 4

Derivation and Validation of the Sepsis Score

The possibility of accurately diagnosing sepsis using the Sepsis Score was tested in two clinical cohorts of patients. This study was approved by the Massachusetts General Hospital Institutional Review Board. Subjects were consenting adults >18 years and <80 years, in two patient cohorts. A "derivation" cohort of 23 patients included trauma and postoperative surgical patients admitted to the surgical intensive care unit (SICU) for trauma or surgical management (injury severity scores greater than 15, critically ill, or postoperative patients with indwelling lines). Data collected from the derivation cohort of patients was used to optimize the analysis and machine learning.

A "validation" cohort of 15 patients (6 septic and 9 non-septic) was then calculated to be sufficient to show that the performance of the assay, as predicted by the derivation cohort, was significantly better than the current sepsis diagnostic standard (sepsis-3, with a 0.05 probability of a type-I error and 90% power). Subsequently, a "validation" cohort of 20 patients admitted to Cardiac, Medical, and Surgical Intensive Care Units was enrolled and used for the blinded validation of the assay. Eleven patients were septic and 9 were non-septic. All blood samples were drawn with consent from patients with existing venous lines expected to remain in place for more than 48 hours.

The first sample was drawn within first 7 days of admission to intensive care. Thereafter, a blood sample was drawn every three days for up to two weeks or until patient was discharged, relocated to another unit, or developed sepsis. During periods of sepsis, samples were drawn daily. Removal of indwelling line automatically excluded (removed) a patient from the study. Sixteen commercial blood samples from healthy donors were used as a non-patient control (Research Blood Components LLC, Allston, Mass.).

Patients were clinically defined as having sepsis when they were found to have a source of infection confirmed by blood, urine, or sputum culture, and evidence of organ dysfunction. If patients who were septic demonstrated signs of inadequate end organ perfusion as evidenced by persistent vasopressor requirement or had an elevated serum lactic acid level despite adequate fluid resuscitation, they were defined as having septic shock. In addition, patients in the first, "derivation" cohort were evaluated based on the older definition of systemic inflammatory response syndrome (SIRS). The SIRS criteria were previously used to define a global inflammatory response, and in the setting of infection, comprised the definition of sepsis. In the setting of the SIRS criteria, septic shock included a lactic acidosis and hypotension despite adequate fluid resuscitation.

The SIRS criteria included:
temperature dysregulation—hyperthermia (>38° C.) or hypothermia (<36° C.),
heart rate >90 beats/minute,
respiratory rate >20 breaths/minute or PaCO2<32 mm Hg, and
WBC >12,000/mm3 or <4,000/mm$^3$ or >10% bands.

Patients in the second, "validation" cohort were evaluated using the recent sepsis-3 guidelines published in 2016, which defined sepsis as end-organ dysfunction caused by the host response to infection. This dysfunction was quantified by the sequential organ failure assessment (SOFA) score, which considers the different organ systems and the degree of dysfunction in each one. Following these recent guidelines, septic shock was defined as hypotension requiring vasopressors to maintain a Mean Arterial Pressure (MAP) greater than 65 mm Hg, and a serum lactic acid above 2 mmol/dL despite adequate fluid resuscitation.

Figures 10A, 10B:
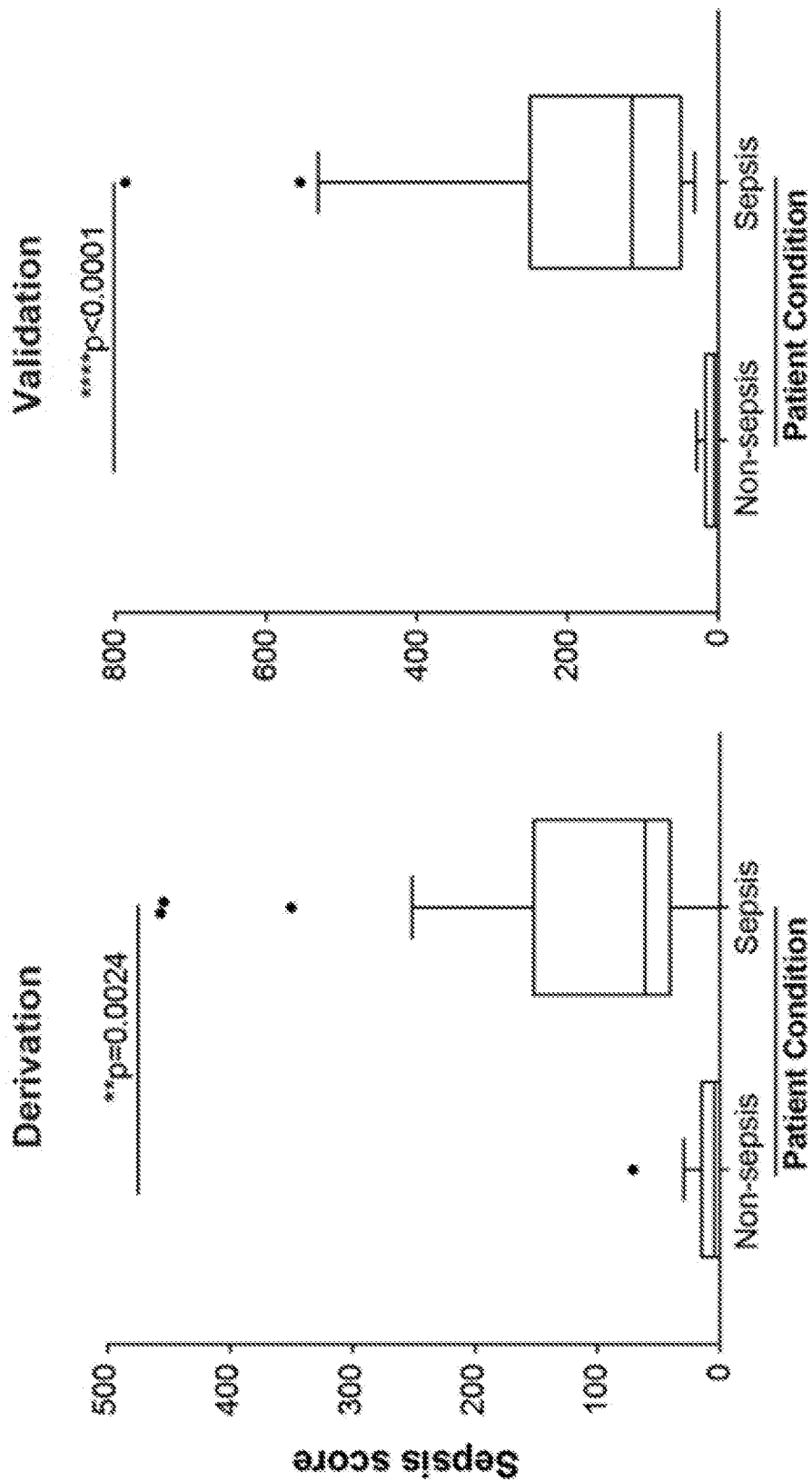
FIGS. 10A and 10B are a pair of boxplots showing the Sepsis Scores for septic and non-septic samples in two independent cohorts of patients.

FIGS. 10A-B are a pair of boxplots showing that the Sepsis Scores were significantly higher for samples from septic versus non-septic patients in both the primary "Derivation" cohort (FIG. 10A, N=87 samples, N=23 patients) and the independent, double-blinded "Validation" cohort (FIG. 10B, N=47 samples, N=20 patients). Box and whisker plots: Tukey's boxplot. Statistics: One-way ANOVA with Tukey's multiple comparison test. Thus, the Sepsis Score was able to accurately diagnose sepsis.

Figure 11:
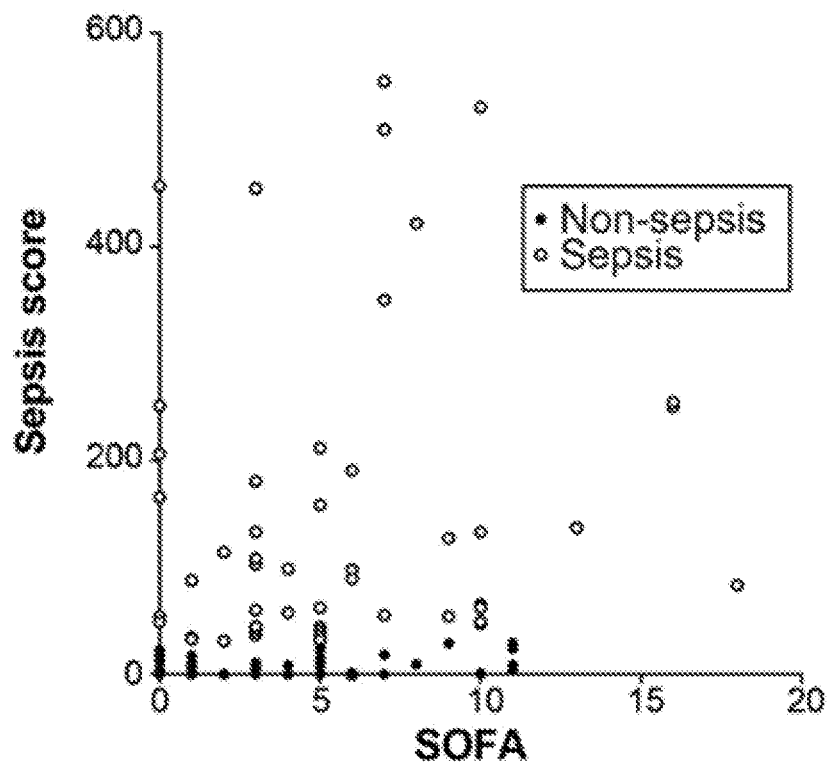
FIG. 11 a scatterplot showing matched SOFA and Sepsis Scores for all patient samples.

FIG. 11 is a scatterplot showing matched SOFA and Sepsis Scores for all patient samples measured in this study. Non-sepsis scores are represented by full circles, while Sepsis samples are shown as empty circles. Samples from non-septic patients all scored below 30, while all septic samples scored above 30. Sepsis was diagnosed with 100% specificity.

Figure 12:
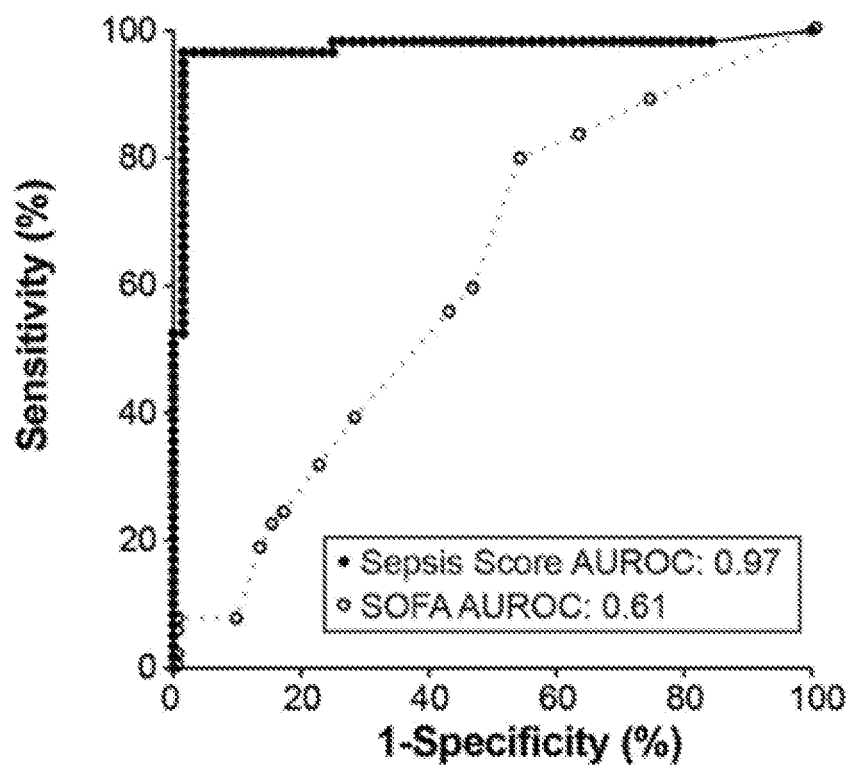
FIG. 12 is a Receiver-Operator Curve (ROC) plot showing the specificity and sensitivity of the Sepsis Score in segregating sepsis samples from non-sepsis samples relative to the SOFA score.

FIG. 12 is a Receiver-Operator Curve (ROC) plot showing the high specificity and sensitivity of the Sepsis Score (full circles, solid line) in correctly segregating Sepsis samples from Non-sepsis samples, compared to the SOFA score (empty circles, dashed line).

The results of FIGS. 10A-B, 11, and 12 show that the Sepsis Score derived from whole blood samples from 43 critically ill patients from two independent patient cohorts can be used to accurately diagnose sepsis. In a first derivation cohort, machine learning approaches were applied to assay results using blood samples collected from 23 trauma and postoperative surgical patients in order to develop a scoring system that effectively segregates patients with sepsis from those without sepsis. In a second validation cohort of 20 cardiac, medical, and surgical intensive care patients, the established scoring system was validated by correctly identifying all septic individuals in a blinded study. Overall, neutrophil spontaneous motility measured from whole blood can diagnose sepsis with 97% sensitivity and 98% specificity in critically ill patients. This represents a significant performance improvement compared to current sepsis diagnostic capabilities and suggests that neutrophils can play more important roles in sepsis than previously appreciated.

Other Embodiments

A number of embodiments of the invention have been described. Nevertheless, it will be understood that various modifications can be made without departing from the spirit and scope of the invention. Accordingly, other embodiments are within the scope of the following claims.

What is claimed is:

1. A microfluidic device comprising:
 (a) a sample loading chamber comprising a plurality of outlets,
 (b) a migration chamber having a plurality of inlets and configured and sized to provide motile cells a choice of directional migration, and
 (c) a plurality of migration channels arranged in fluid communication between the outlets of the sample loading chamber and the inlets of the migration chamber, wherein each migration channel is connected to enable a sample to flow from an outlet of the sample loading chamber to an inlet of the migration chamber, wherein all migration channels are connected to the same migration chamber, and wherein the migration chamber comprises a maze chamber.

2. The microfluidic device of claim 1, wherein the migration channels are sized to allow the migration of neutrophils.

3. The microfluidic device of claim 1, wherein inlet ends of the migration channels are sized to exclude red blood cells to a greater extent than neutrophils from entering the migration channels.

4. The microfluidic device of claim 1, further comprising a baffle arranged in fluid communication between the outlets of the sample loading chamber and the migration channels or within the migration channels, but at a point before each migration channel enters an inlet of the migration chamber.

5. The microfluidic device of claim 4, wherein the baffle comprises one or more passageways configured to inhibit the movement of red blood cells through the baffle to a greater extent than the baffle inhibits movement of the neutrophils through the baffle.

6. The microfluidic device of claim 5, wherein a cross-sectional area of the baffle passageway normal to the sample transport path in the baffle passageway is less than a red blood cell cross-sectional area, and wherein a width of the cross-sectional area is less than a red blood cell diameter.

7. The microfluidic device of claim 4, further comprising an exit channel in fluid communication with the migration channel at a point beyond the baffle and before the migration channel enters the inlet of the migration chamber.

8. The microfluidic device of claim 1 wherein the cross-sectional area of the migration channels or baffle passageways is greater than a red blood cell cross-sectional area, and wherein one or more migration channels or baffle passageways have at least one turn, such that red blood cells are prevented from moving past the turn.

9. The microfluidic device of claim 4, wherein the device comprises:
a plurality of baffle passageways; and
a plurality of migration channels;
wherein each baffle passageway is in fluid communication with a migration channel, and
wherein the migration channels and the migration chamber each comprise a transparent cover material to enable motility of neutrophils to be monitored in the migration channels and the migration chamber.

10. The microfluidic device of claim 1, wherein the microfluidic device comprises a substrate, and wherein the chambers and channels of the device are arranged in fluid communication on the substrate.

11. The microfluidic device of claim 1, further comprising a buffer liquid that includes no exogenous chemical attractant.

12. A method of monitoring the motility of neutrophils in the microfluidic device of claim 1, the method comprising:
(a) adding a blood sample to the sample loading chamber of the microfluidic device;
filling the microfluidic device with a buffer liquid that includes no exogenous chemical attractant; and
(b) monitoring spontaneous motility of one or more neutrophils in the one or more migration channels in the absence of an exogenously added chemical attractant gradient.

13. The method of claim 12,
further comprising incubating the microfluidic device under conditions and for a time sufficient to enable movement of neutrophils in the sample from the sample loading chamber into the one or more migration channels; and
monitoring spontaneous motility of one or more neutrophils in the one or more migration channels and the migration chamber.

14. The method of claim 12, wherein the microfluidic device further comprises a baffle arranged in fluid communication between the outlet of the sample loading chamber and the one or more migration channel or within the migration channel, but a point before the migration channels enter the inlet of the migration chamber, wherein the baffle comprises a passageway configured to inhibit the movement of red blood cells through the baffle to a greater extent than the baffle inhibits movement of the neutrophils through the baffle.

15. The method of claim 12, wherein monitoring the motility of neutrophils comprises quantifying one or more of velocity, migration distance, migration direction, velocity persistence, and directional persistence of neutrophils in the one or more migration channels.

16. The method of claim 12, wherein monitoring the motility of neutrophils comprises quantifying two or more neutrophil motility parameters selected from the group consisting of:
(a) number of spontaneously migrating neutrophils;
(b) number of neutrophils that undergo a migratory oscillation;
(c) number of neutrophils that undergo a migratory pause;
(d) whether neutrophils reverse their migration;
(e) average distance migrated by neutrophils;
(f) maximum migration distance;
(g) mean velocity of neutrophils;
(h) mean acceleration of neutrophils;
(i) mean distance of oscillatory migration;
(j) mean forward migration of neutrophils away from the migration chamber entrance;
(k) mean vertical migration of neutrophils parallel to the migration channels;
(l) mean horizontal migration of neutrophils perpendicular to the migration channels; and
(m) mean nucleus size of migrating neutrophils.

17. The method of claim 16, further comprising determining a sepsis score by combining the quantified results for the neutrophil motility parameters; and wherein a sepsis score that is above a certain threshold indicates that the subject has sepsis or will develop sepsis.

18. The method of claim 17, wherein a sepsis score is determined using the following formula:

$$\text{Sepsis Score} = \frac{N(O + P + R + AD)}{10^3},$$

wherein N is the number of spontaneously migrating neutrophils, O is the number of neutrophils that undergo a migratory oscillation, P is the number of neutrophils that undergo a migratory pause, R is the number of neutrophils that reverse migration, and AD is the average distance traveled by the neutrophils.

19. A method of diagnosing sepsis in a subject, the method comprising:
(a) obtaining a device of claim 1;
(b) adding a blood sample to the sample loading chamber;
(c) incubating the device under conditions and for a time sufficient to enable movement of cells in the sample from the sample loading chamber into the migration channel; and
(d) monitoring motility of one or more neutrophils in the migration channel and/or the migration chamber;
wherein monitoring the motility of neutrophils comprises quantifying the following neutrophil motility parameters:
number of spontaneously migrating neutrophils;
number of neutrophils that undergo a migratory oscillation;
number of neutrophils that undergo a migratory pause;
whether neutrophils reverse their migration; and
average distance migrated by neutrophils; and
(e) determining a sepsis score by combining the quantified results for the neutrophil motility parameters using the formula $$\text{Sepsis Score} = \frac{N(O + P + R + AD)}{10^3},$$

wherein a sepsis score that is 30 or above indicates that the subject has sepsis.

* * * * *

UNITED STATES PATENT AND TRADEMARK OFFICE
CERTIFICATE OF CORRECTION

Page 1 of 1

PATENT NO. : 11,130,132 B2
APPLICATION NO. : 16/099117
DATED : September 28, 2021
INVENTOR(S) : Daniel Irimia, Felix Ellett and Julianne Jorgensen It is certified that error appears in the above-identified patent and that said Letters Patent is hereby corrected as shown below:

In the Specification

Column 1, Line 15, insert -- STATEMENT OF FEDERALLY SPONSORED RESEARCH
This invention was made with government support under Grant No. GM092804 awarded by the National Institutes of Health. The government has certain rights in the invention. --

Signed and Sealed this
Twenty-third Day of May, 2023

Katherine Kelly Vidal
*Director of the United States Patent and Trademark Office*